United States Patent
Yanagisawa et al.

(10) Patent No.: US 8,512,597 B2
(45) Date of Patent: Aug. 20, 2013

(54) POLYMERIZABLE OPTICALLY ACTIVE IMIDE COMPOUND AND POLYMERIZABLE COMPOSITION CONTAINING THE COMPOUND

(75) Inventors: Satoshi Yanagisawa, Tokyo (JP); Masatomi Irisawa, Tokyo (JP)

(73) Assignee: Adeka Corporation, Tokyo (JP)

( * ) Notice: Subject to any disclaimer, the term of this patent is extended or adjusted under 35 U.S.C. 154(b) by 21 days.

(21) Appl. No.: 13/003,796

(22) PCT Filed: Aug. 25, 2009

(86) PCT No.: PCT/JP2009/064801
§ 371 (c)(1),
(2), (4) Date: Jan. 12, 2011

(87) PCT Pub. No.: WO2010/032591
PCT Pub. Date: Mar. 25, 2010

(65) Prior Publication Data
US 2011/0108765 A1    May 12, 2011

(30) Foreign Application Priority Data
Sep. 18, 2008 (JP) ................................. 2008-238996

(51) Int. Cl.
- C09K 19/00 (2006.01)
- C09K 19/52 (2006.01)
- C09K 19/06 (2006.01)
- C09K 19/34 (2006.01)
- G02F 1/1333 (2006.01)
- C08F 22/40 (2006.01)
- C07D 207/00 (2006.01)

(52) U.S. Cl.
USPC ............... 252/299.61; 252/299.01; 252/299.6

(58) Field of Classification Search
USPC ............. 252/299.01, 299.6, 299.61; 428/1.1; 349/1, 182; 526/72, 258, 262; 548/400, 548/541, 543, 544
See application file for complete search history.

(56) References Cited

U.S. PATENT DOCUMENTS

| | | | |
|---|---|---|---|
| 4,996,330 A | 2/1991 | Scherowsky et al. | |
| 5,258,134 A | 11/1993 | Yoshinaga et al. | |
| 5,502,206 A | 3/1996 | Zahn et al. | |
| 5,780,629 A | 7/1998 | Etzbach et al. | |
| 6,423,246 B1 * | 7/2002 | Kasch et al. | 252/299.01 |
| 6,723,395 B2 | 4/2004 | May et al. | |

FOREIGN PATENT DOCUMENTS

| | | |
|---|---|---|
| EP | 03-99279 | 9/1995 |
| JP | 2-053768 | 2/1990 |
| JP | 4-317025 | 11/1992 |
| JP | 2003-055661 | 2/2003 |
| JP | 2003-313250 | 11/2003 |
| JP | 2005-281223 | 10/2005 |
| WO | 2006/120220 | 11/2006 |

OTHER PUBLICATIONS

International Search Report—PCT/JP2009/064801—Oct. 13, 2009.
Galatina, A.I. et al,—The synthesis and structure of 1, 3, 4-trisubstituted 2, 5-dioxopyrrolidines and their behavior in liquid crystalline systems, Liquid Crystals—2000—vol. 27, No. 9, p. 1229-1233, full text, particulary, Scheme 1.
CN Office Action dated May 4, 2012, with English Translation.

* cited by examiner

*Primary Examiner* — Geraldina Visconti
(74) *Attorney, Agent, or Firm* — Young & Thompson

(57) ABSTRACT

A polymerizable optically-active imide compound represented by the following general formula (I). Preferable among the polymerizable optically-active imide compound are compounds wherein $X^3$ and $X^4$ in general formula (I) are both —CO—, compounds wherein the rings $A^2$ and $A^3$ in general formula (I) are both naphthalene rings, compounds wherein the rings $A^1$, $A^2$, $A^3$, and $A^4$ are all benzene rings, compounds wherein $M^1$ and $M^2$ in general formula (I) are both hydrogen atoms, or compounds wherein rings $A^1$ and $A^4$, as well as rings $A^2$ and $A^3$, in general formula (I) are the same ring, the groups $M^1$ and $M^2$, $X^1$ and $X^6$, $X^2$ and $X^5$, as well as $X^3$ and $X^6$ are the same group in each pair, and n and m are the same number.

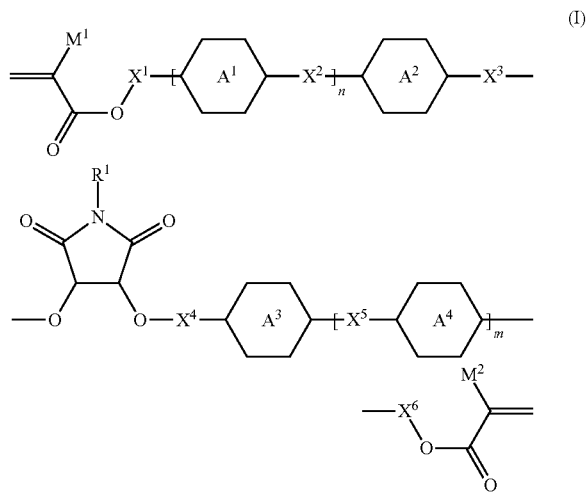

23 Claims, No Drawings

POLYMERIZABLE OPTICALLY ACTIVE IMIDE COMPOUND AND POLYMERIZABLE COMPOSITION CONTAINING THE COMPOUND

TECHNICAL FIELD

The invention relates to a novel polymerizable optically-active imide compound, a polymerizable composition containing the compound, and a polymer prepared by photocuring the polymerizable composition. More particularly, the invention relates to a polymerizable optically-active imide compound having a cyclic imide structure as an optically-active moiety and having a (meth)acryloyloxy group as a polymerizable moiety, and also to a polymerizable composition and a polymer prepared using the compound. The polymer of the invention is useful for optically anisotropic elements, such as polarizers, retardation films, optical compensation films such as negative C-plates, visual compensation films, luminance improving films, and reflective films.

BACKGROUND ART

Recent liquid crystal displays, such as liquid crystal TV monitors and video camcorder monitors, are required to operate at low voltages with low power consumption. To meet such demands, studies are being made of the use of optically anisotropic elements—e.g., retardation films, polarizers, polarizing prisms, or reflective films, which make use of the orientation characteristics and anisotropic physical properties of liquid crystal substances, such as refractive index, dielectric constant, and magnetic susceptibility—as means for increasing light source utilization or for improving viewing angle characteristics of LCD elements.

Such an optically anisotropic element can be obtained by polymerizing a liquid crystal compound having a polymerizable moiety, or a polymerizable composition containing a liquid crystal compound having a polymerizable moiety, through irradiation with energy rays such as ultraviolet rays, while keeping the compound/composition in a certain orientation. In other words, the resulting optically anisotropic element is fixed while maintaining its molecular orientation, and is designed to exhibit optical anisotropy owing to its conformationally-controlled optically-active moiety.

In particular, adding an optically-active compound to a liquid crystal composition induces the liquid crystal molecules to take on a helical structure, which allows manipulation of the optical properties of the resulting optically anisotropic element. The periodic length, i.e., the helical pitch, of the helical structure depends on the helical twisting power inherent to each optically-active compound and the amount of compound added. An optically-active compound having low helical twisting power can induce only a long helical pitch in the liquid crystal compound. So, if there is a need for a shorter helical pitch, then the optically-active compound must be added in larger amounts. However, an increase in the amount of optically-active compound added generally impairs the performance properties as a liquid crystal material, which can result in various problems, such as increase in viscosity, decrease in response speed, increase in driving voltage, narrowing of temperature range for the liquid crystal phase to occur, and drop in isotropic phase transition temperature. Accordingly, there has been a demand for an optically-active compound with higher helical twisting power.

However, none of the optically-active compounds hitherto reported is satisfactory (see, e.g. Patent Document 1 to 7). Patent Document 8 discloses substituted tartarimide derivatives, but discloses nothing about compounds having polymerizable groups. Patent Document 9 discloses introduction of a tartarimide derivative having a polymerizable group to an organosiloxane, but discloses nothing about a compound that may be used for the above-described purposes.

CITATION LIST

Patent Document

Patent Document 1: U.S. Pat. No. 5,258,134 A
Patent Document 2: EP 0399279 B1
Patent Document 3: JP-A-4-317025
Patent Document 4: U.S. Pat. No. 5,780,629 A
Patent Document 5: JP-A-2003-55661
Patent Document 6: US 2003026922 A1
Patent Document 7: JP-A-2005-281223
Patent Document 8: U.S. Pat. No. 4,996,330 A
Patent Document 9: U.S. Pat. No. 5,502,206 A

SUMMARY OF THE INVENTION

Problems to be Solved by the Invention

Accordingly, the present invention aims at providing an optically-active compound that has high helical twisting power and that can be added to a liquid crystal composition to achieve the required helical pitch without significantly impairing the physical and optical properties of the liquid crystal composition.

Means for Solving the Problems

The invention achieves the above object through provision of a polymerizable optically-active imide compound represented by the following general formula (I):

[Chem. 1]

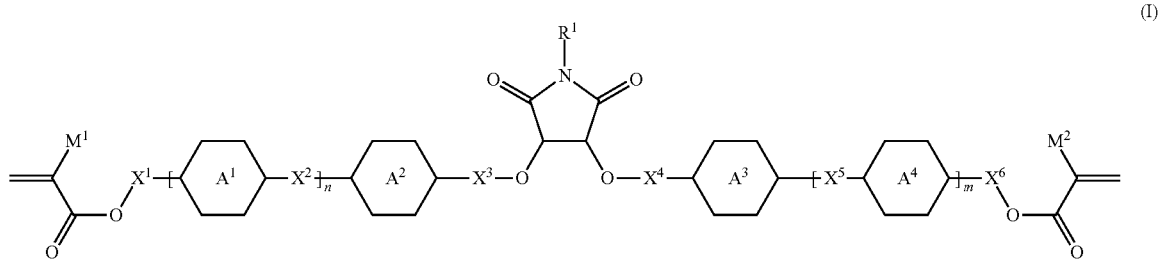

(I)

wherein, rings $A^1$, $A^2$, $A^3$, and $A^4$ each independently represent a benzene ring or a naphthalene ring, wherein a carbon atom in the benzene ring and the naphthalene ring may optionally be substituted by a nitrogen atom; $M^1$ and $M^2$ each independently represent a hydrogen atom or a methyl group; $R^1$ represents a $C_{1-10}$ alkyl group, a $C_{6-20}$ aryl group, or a $C_{7-20}$ arylalkyl group; a hydrogen atom in $R^1$ may optionally be substituted by a halogen atom; the methylene group in $R^1$ may be interrupted by —O—, —COO—, or —COO—; $X^1$ represents a direct bond, -$L^1$-, -$L^1$O—, -$L^1$O—CO—, -$L^1$CO—O—, or -$L^1$O—CO—O—; $X^2$ and $X^5$ each independently represent a linking group consisting of a direct bond, an ester bond, an ether bond, a $C_{1-8}$ alkylene group that may be branched and that may have an unsaturated bond, or a combination thereof; $X^3$ represents a direct bond, —CO—, -$L^2$-, —O$L^2$-, —O—CO$L^2$-, —CO—O$L^2$-, or —O—CO—O$L^2$-; $X^4$ represents a direct bond, —CO—, -$L^1$-, -$L^1$O—, -$L^1$O—CO—, -$L^1$CO—O—, or -$L^1$O—CO—O—; $X^6$ represents a direct bond, -$L^2$-, —O$L^2$-, —O—CO$L^2$-, —CO—O$L^2$-, or —O—CO—O$L^2$-; $L^1$ and $L^2$ each independently represent a $C_{1-8}$ alkylene group that may be branched, wherein the alkylene group may be interrupted one to three times by an oxygen atom; and n and m each independently represent 0 or 1.

The present invention also provides a polymerizable composition containing the above polymerizable optically-active imide compound and optionally containing a liquid crystal compound as necessary.

The present invention also provides a polymer prepared by photopolymerization of the above polymerizable composition, and an optical film made using the polymer.

Effects of the Invention

The polymerizable optically-active imide compound of the invention is novel, and even a slight amount thereof will allow the reflection wavelength of a liquid crystal composition, particularly a cholesteric liquid crystal composition, to be shifted toward the shorter-wavelength side. Further, the wavelength range of selectively-reflected light of the present polymerizable optically-active imide compound can be adjusted simply by changing the mesogenic structure of the compound. Furthermore, the present optically-active compound can suitably be used as a chiral dopant in polarizers and optical films.

BEST MODE FOR CARRYING OUT THE INVENTION

The polymerizable optically-active imide compound of the invention, the polymerizable composition of the invention containing the present polymerizable optically-active imide compound, and the polymer of the invention prepared by photopolymerization of the present polymerizable composition will be described in detail below according to preferred embodiments thereof.

First, the polymerizable optically-active imide compound of the invention will be described.

Examples of the $C_{1-10}$ alkyl group represented by $R^1$ in general formula (I) include methyl, ethyl, propyl, isopropyl, butyl, s-butyl, t-butyl, isobutyl, amyl, isoamyl, t-amyl, hexyl, cyclohexyl, heptyl, isoheptyl, t-heptyl, n-octyl, isooctyl, t-octyl, and 2-ethylhexyl; examples of the $C_{6-20}$ aryl group include phenyl, naphthyl, 2-methylphenyl, 3-methylphenyl, 4-methylphenyl, 4-vinylphenyl, and 3-isopropylphenyl; and examples of the $C_{7-20}$ arylalkyl group include benzyl, phenethyl, 2-phenylpropan-2-yl, diphenylmethyl, triphenylmethyl, styryl, and cinnamyl. A hydrogen atom in the above substituents may be substituted by a halogen atom, such as fluorine, chlorine, bromine, or iodine, and the methylene group in the above substituents may be interrupted by —O—, —COO—, or —OCO—.

Examples of the $C_{1-8}$ alkylene group represented by $X^2$, $X^5$, $L^1$, and $L^2$ in general formula (I) include methylene, ethylene, propylene, trimethylene, tetramethylene, 1,3-butanediyl, 2-methyl-1,3-propanediyl, 2-methyl-1,3-butanediyl, 2,4-pentanediyl, 1,4-pentanediyl, 3-methyl-1,4-butanediyl, 2-methyl-1,4-pentanediyl, pentamethylene, hexamethylene, heptamethylene, and octamethylene. The alkylene group may be interrupted one to three times by an oxygen atom.

Polymerizable optically-active imide compounds wherein $X^3$ and $X^4$ in general formula (I) are both —CO— are preferable because of advantages in terms of productivity and because of their high chemical and thermal stability. Even more preferable are polymerizable optically-active imide compounds wherein the rings $A^2$ and $A^3$ in general formula (I) are both naphthalene rings, or polymerizable optically-active imide compounds wherein the rings $A^1$, $A^2$, $A^3$, and $A^4$ are all benzene rings, because of their good compatibility with base liquid crystals.

Further, preferable are polymerizable optically-active imide compounds wherein $M^1$ and $M^2$ in general formula (I) are both hydrogen atoms, because of their high polymerization reactivity and high dissolubility to solvents. Also preferable are polymerizable optically-active imide compounds wherein rings $A^1$ and $A^4$, as well as rings $A^2$ and $A^3$, in general formula (I) are the same ring, the groups $M^1$ and $M^2$, $X^1$ and $X^6$, $X^2$ and $X^5$, as well as $X^3$ and $X^6$ are the same group in each pair, and n and m are the same number, because of advantages in terms of productivity and cost.

Even more preferable are polymerizable optically-active imide compounds wherein $X^1$ and $X^6$ are optionally-branched $C_{1-8}$ alkylene groups, because such compounds are easy to produce.

The compound of the present invention is optically active. "Optically active" means that the compound can cause rotary polarization, which causes linear polarization to be rotated as it passes through the compound. Therefore, among the compounds represented by general formula (I) above, compounds exhibiting dextrorotation or levorotation in optical rotation measurement are the optically-active compounds of the present invention.

The following compounds are examples showing concrete structures of the polymerizable optically-active imide compound of the present invention represented by general formula (I) above. The present invention, however, is not to be limited by the following compounds.

[Chem. 2]

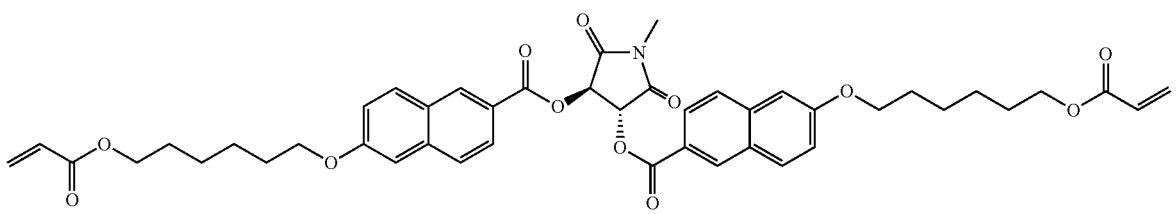

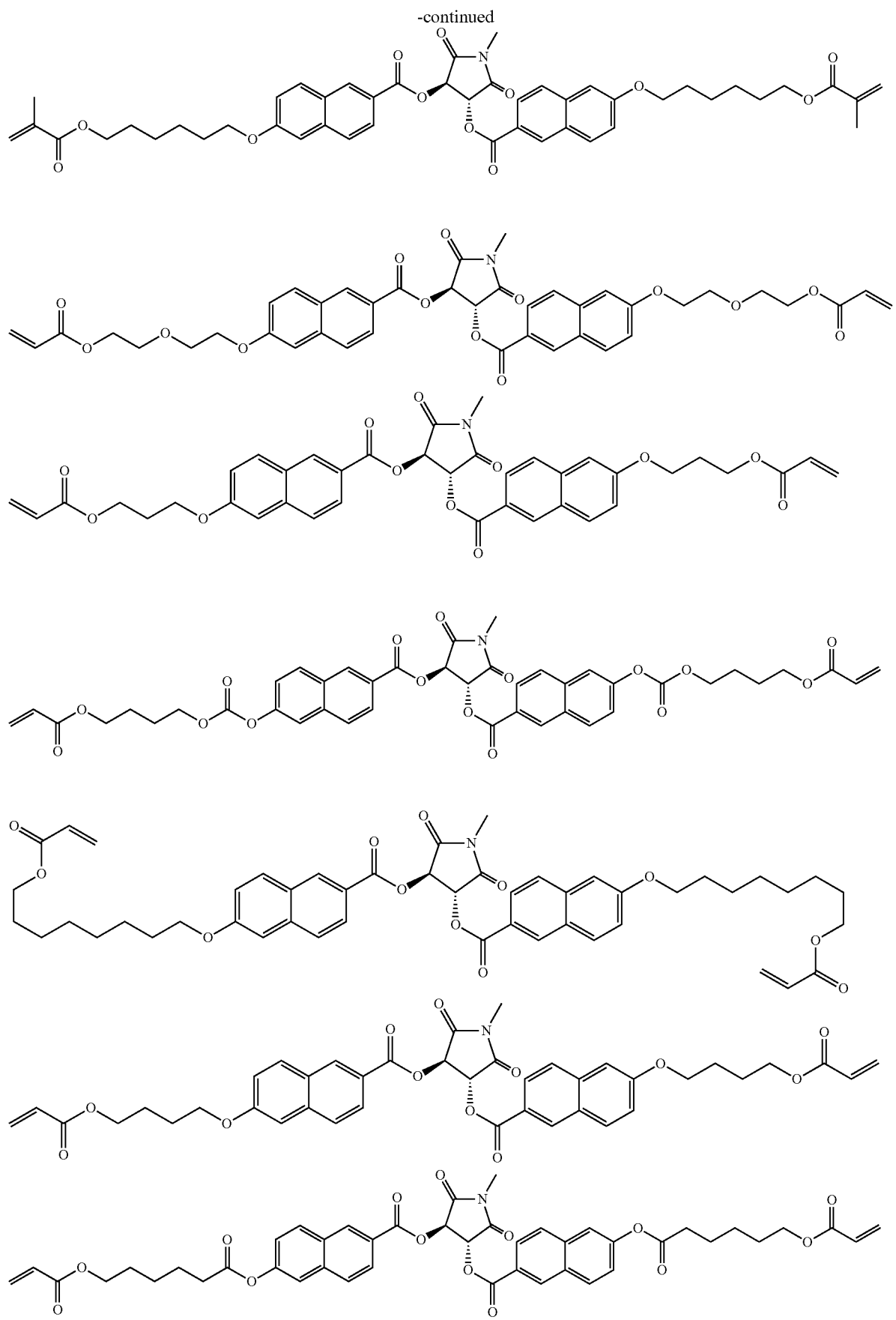

-continued
[Chem. 3]
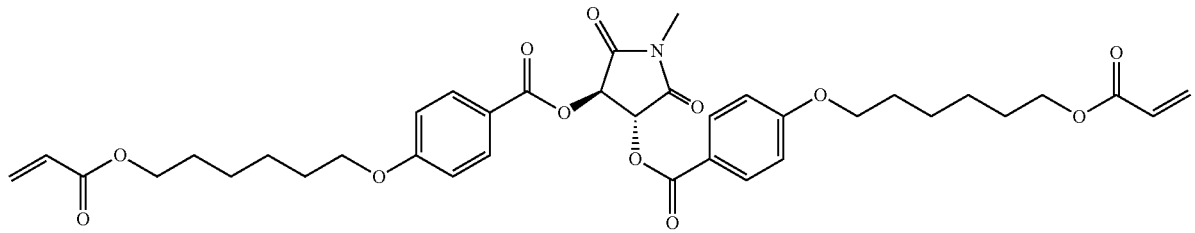
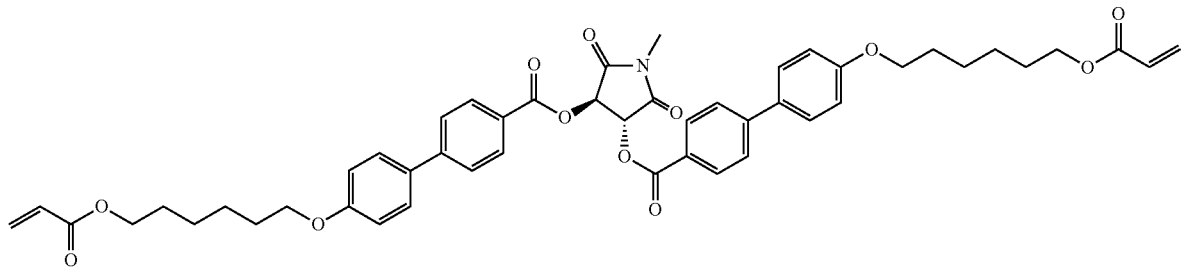
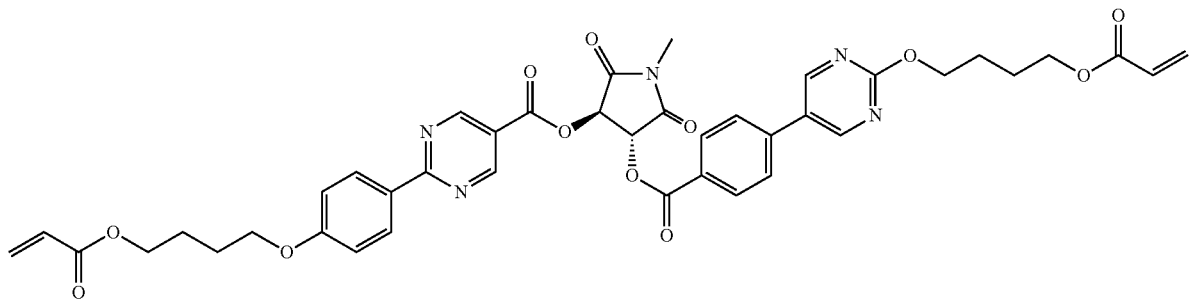
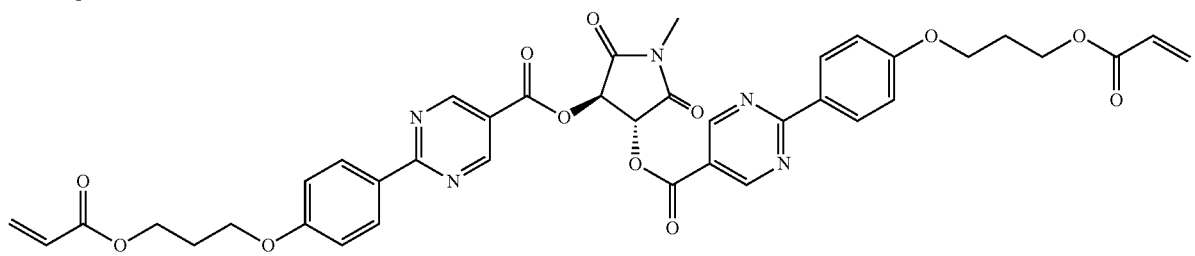
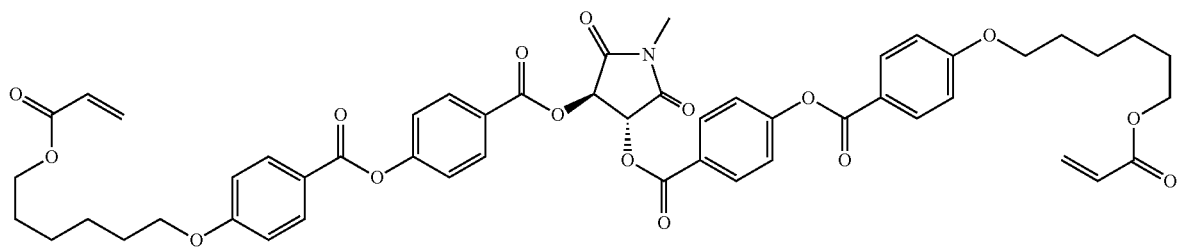
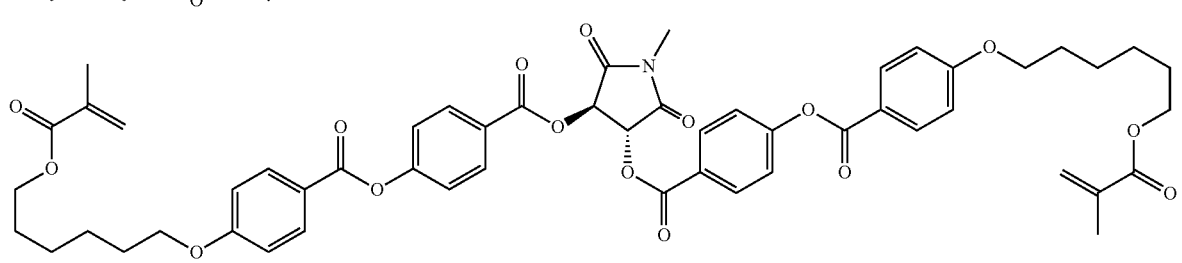

9 10
-continued
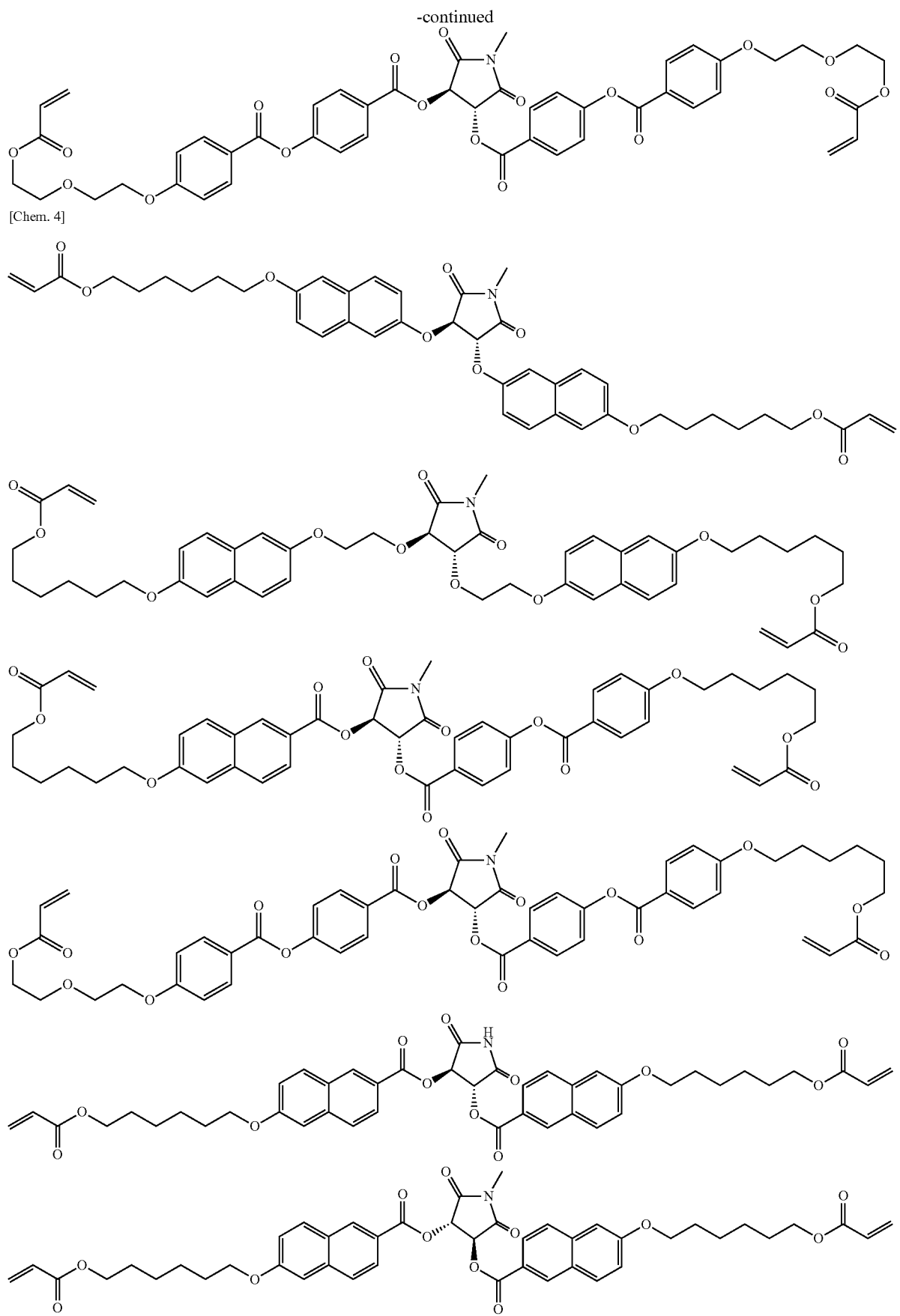

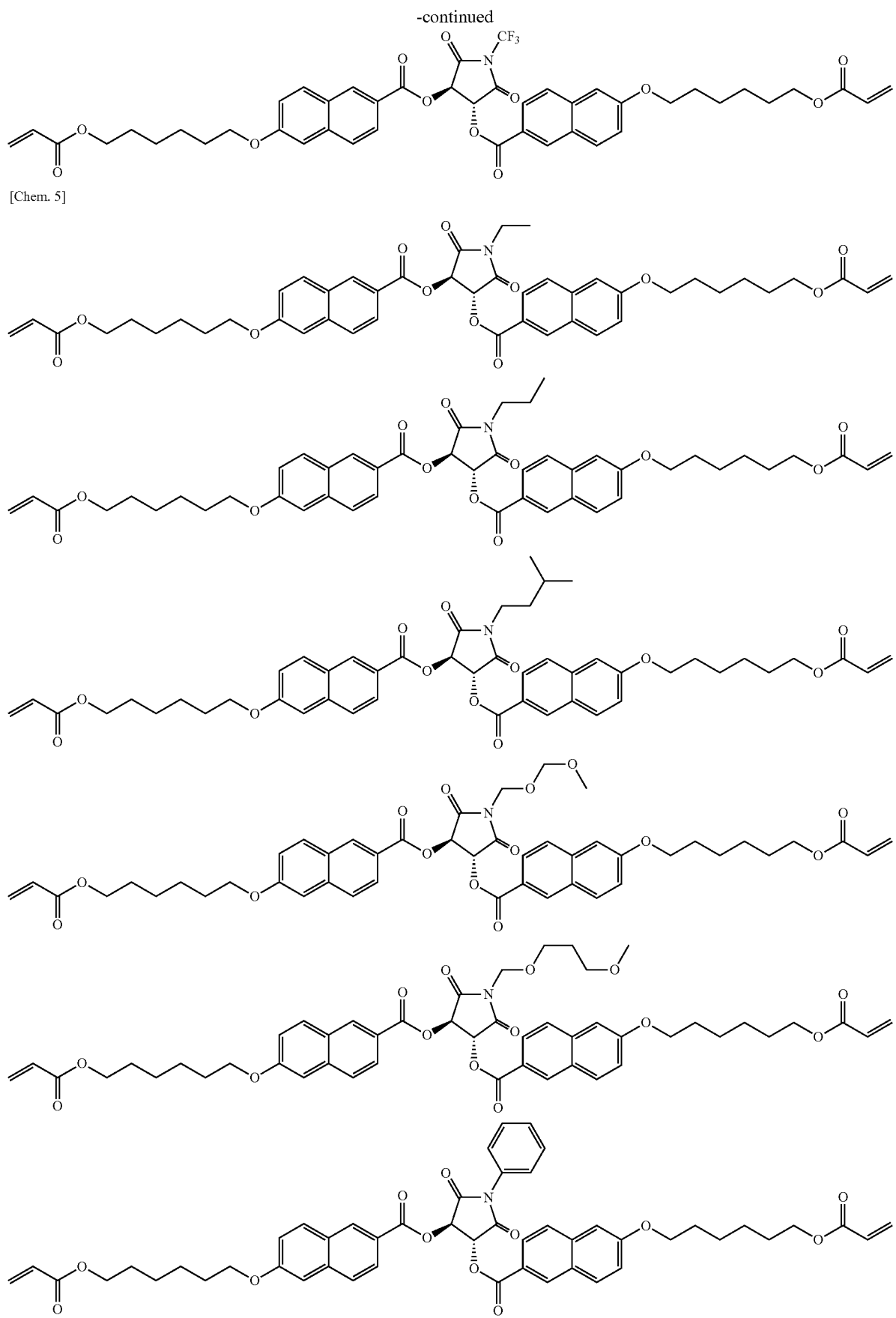

-continued
[Chem. 6]
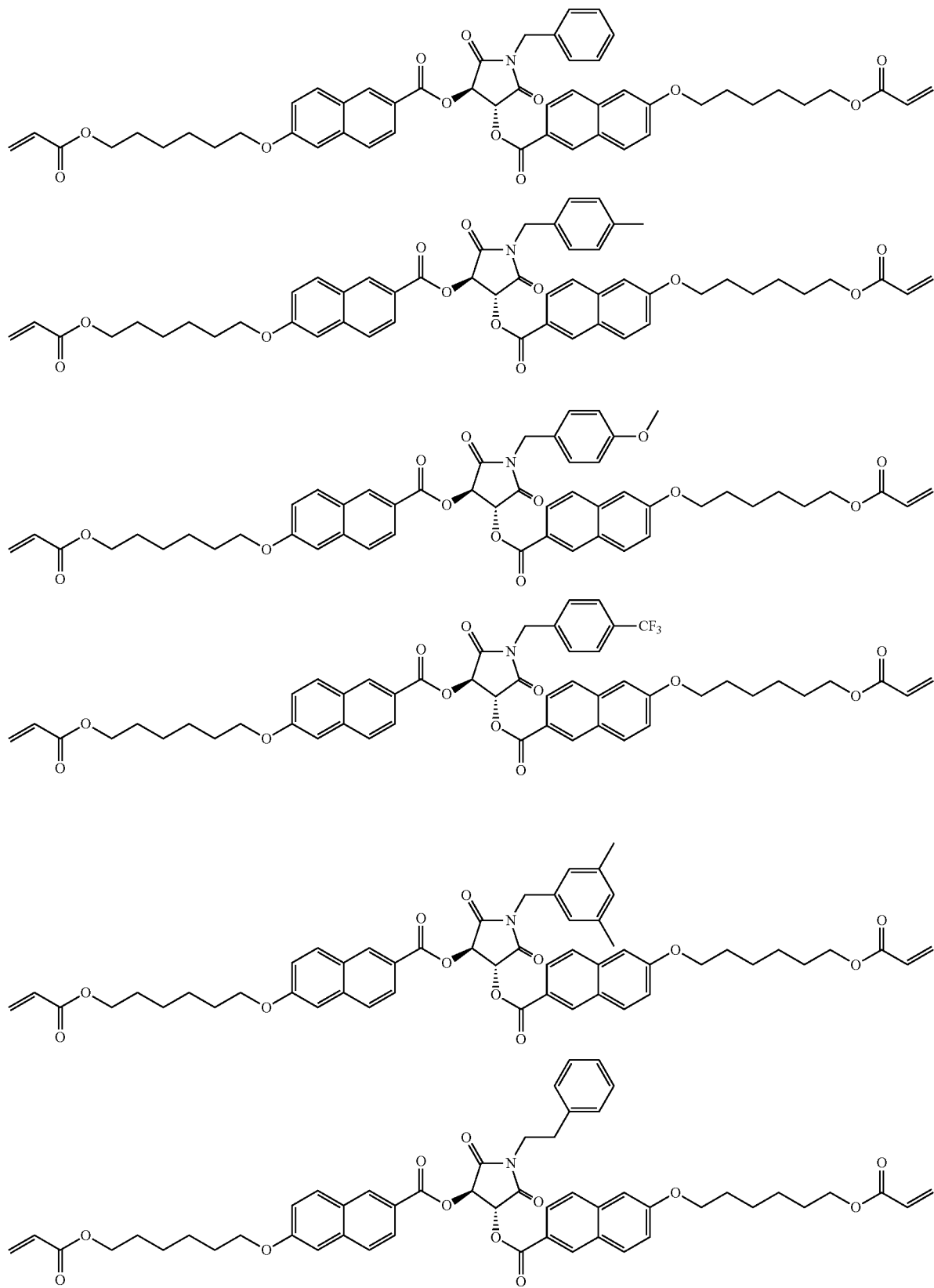

There is no particular limitation to the process for producing the polymerizable optically-active imide compound of the invention, and any known reaction may be applied to the production process thereof. For example, the present compound may be prepared through a dehydration-condensation reaction using a condensation agent according to the equation shown in Chem. 7 below.

[Chem. 7]

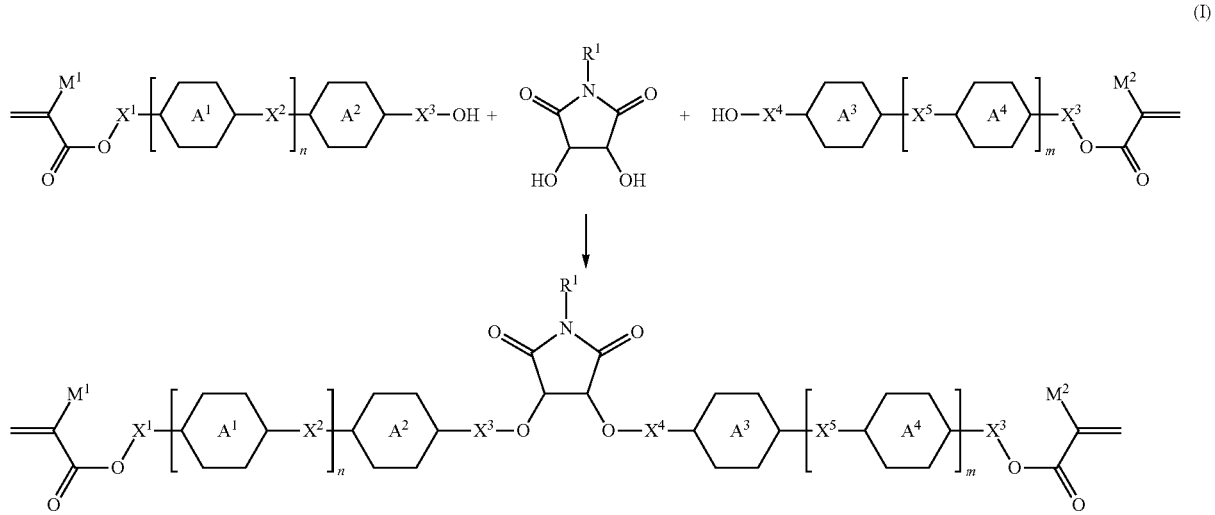

More specifically, a polymerizable optically-active imide compound (II) of the invention can be produced according to the equation shown, for example, in Chem. 8 below by reacting a benzoic acid derivative with a tartarimide derivative in the presence of p-toluenesulfonic acid (TsCl) and N-methylimidazole (NMI).

[Chem. 8]

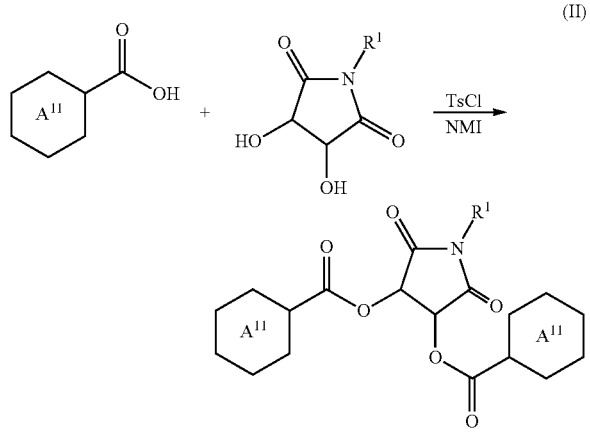

In the equation, ring $A^{11}$ represents a benzene ring or a naphthalene ring having a substituent corresponding to that in general formula (I) above, and $R^1$ is the same as in general formula (I).

The optical purity of the polymerizable optically-active imide compound of the invention prepared through the above process depends on the optical purity of tartaric acid used as the starting material for preparing the tartarimide derivative. Because both enantiomers of tartaric acid can be prepared easily, the polymerizable optically-active imide compound of the invention can be prepared with high optical purity.

The polymerizable optically-active imide compound of the invention can suitably be used as a material for preparing an optically anisotropic element excellent in heat resistance, solvent resistance, transparency, optical properties, and liquid crystal orientation fixing ability by being blended with a liquid crystal material, particularly with a liquid crystal material exhibiting a cholesteric phase. The present imide compound may also be used for liquid crystal orientation films, liquid crystal orientation controlling agents, coating materials, and materials for preparing protective films.

Next, the polymerizable composition of the invention will be described below.

The polymerizable composition of the invention contains the present polymerizable optically-active imide compound. In cases where the present polymerizable composition further contains a liquid crystal compound, it can suitably be used as a material for preparing an optically anisotropic element. The term "liquid crystal compound" as used herein includes known liquid crystal compounds, known liquid-crystal-like compounds, and mixtures thereof.

There is no particular limitation to the blending rate at which the polymerizable optically-active imide compound of the invention and the liquid crystal compound are blended in the polymerizable composition of the invention, as long as curing of the present polymerizable optically-active imide compound is not impaired. Preferably, the content of the polymerizable optically-active imide compound of the invention is 1 to 50 parts by mass, more preferably 1 to 30 parts by mass, per a total of 100 parts by mass of the imide compound and the liquid crystal compound. A rate of less than 1 part by mass of the present polymerizable optically-active imide compound may not be able to achieve the effects of the invention, whereas an amount exceeding 50 parts by mass may give rise to whitish clouding caused by precipitation of the polymerizable optically-active imide compound and non-uniformity in orientation of the liquid crystal molecules, or may cause phase separation, at the time of curing the polymerizable composition.

Any commonly-used liquid crystal compound may be employed as the present liquid crystal compound, and concrete examples include, but are not limited to, the liquid crystal compounds shown in Chem. 9 and Chem. 10 below. In Chem. 9 and Chem. 10, $W^1$ represents a hydrogen atom, an optionally-branched $C_{1-8}$ alkyl group, an optionally-branched $C_{1-8}$ alkoxy group, an optionally-branched $C_{1-8}$ alkenyl group, an optionally-branched $C_{1-8}$ alkenyloxy group, an optionally-branched $C_{1-8}$ alkynyl group, an optionally-branched $C_{1-8}$ alkynyloxy group, an optionally-branched $C_{1-8}$ alkoxyalkyl group, an optionally-branched $C_{1-8}$ alkanoyloxy group, or an optionally-branched $C_{1-8}$ alkoxycarbonyl group, wherein the above-mentioned groups may optionally be substituted by a halogen atom, a cyano group, etc. $W^2$ represents a cyano group, a halogen atom, or a group represented by $W^1$. $W^3$, $W^4$, and $W^5$ each independently represent a hydrogen atom, a halogen atom, or a cyano group.

[Chem. 9]

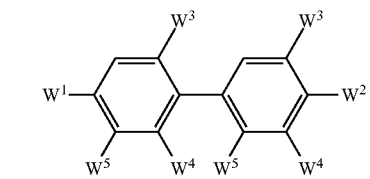

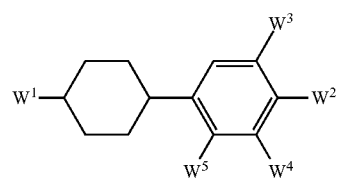

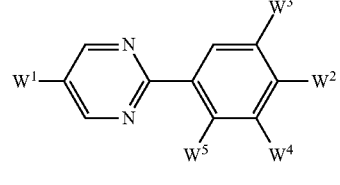

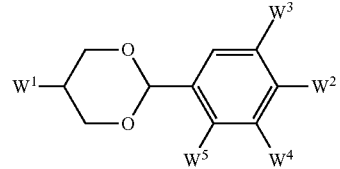

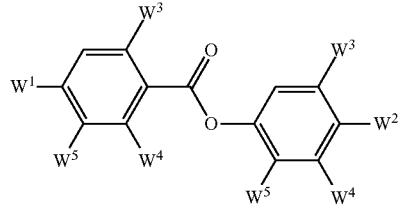

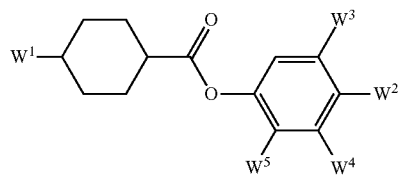

-continued

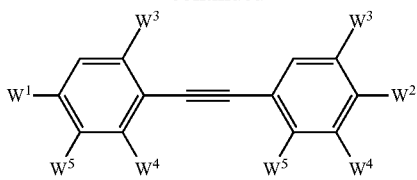

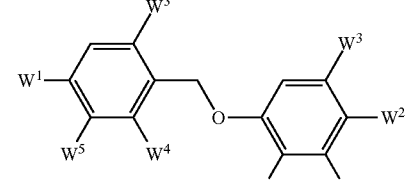

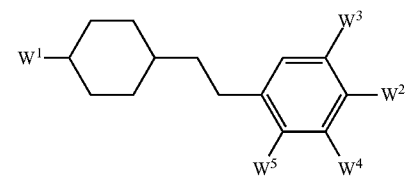

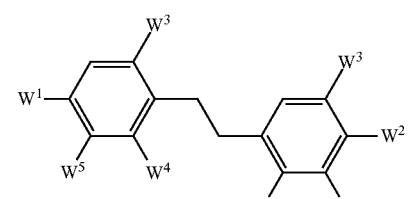

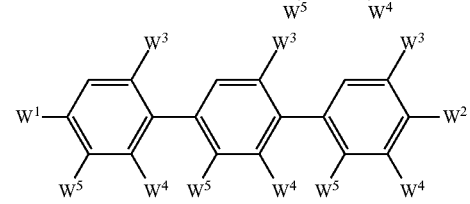

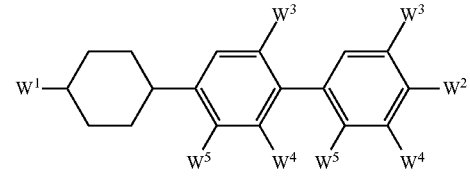

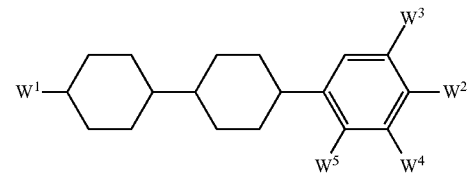

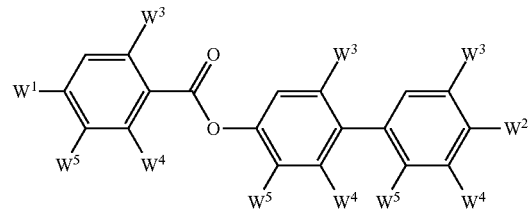

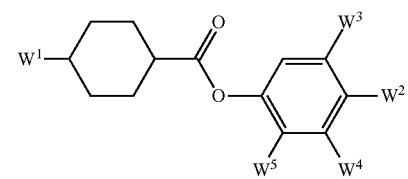

-continued

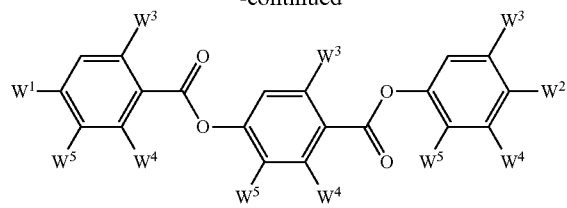
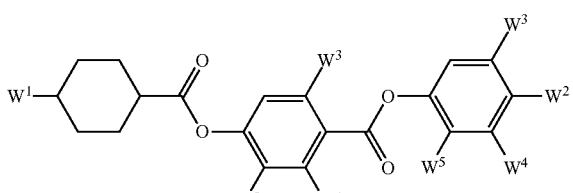
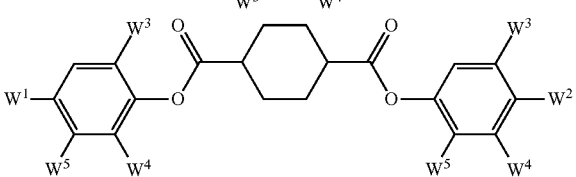
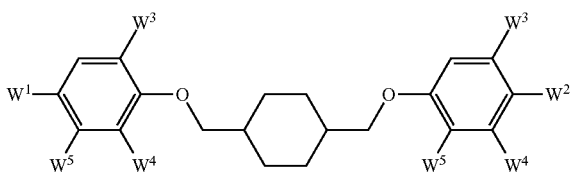
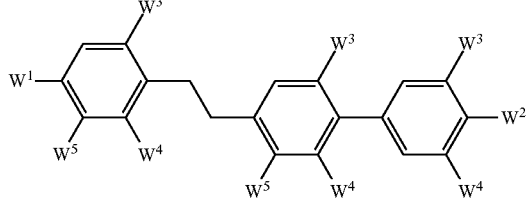
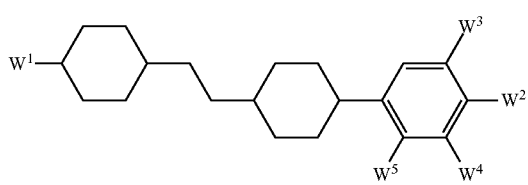

[Chem. 10]

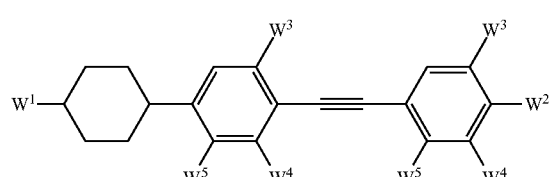
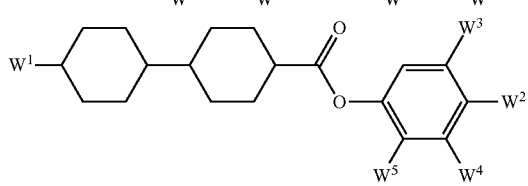

-continued

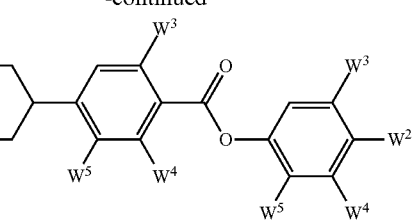
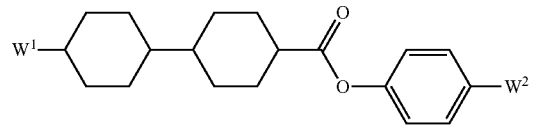
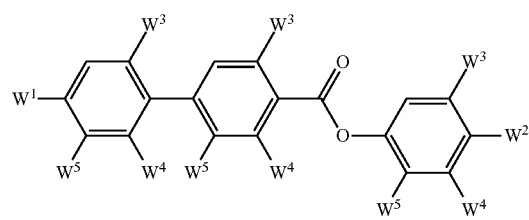
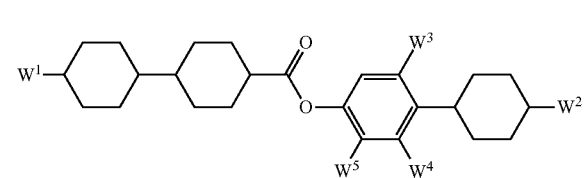
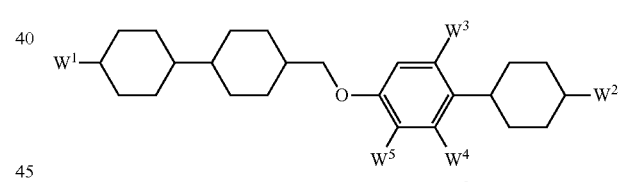
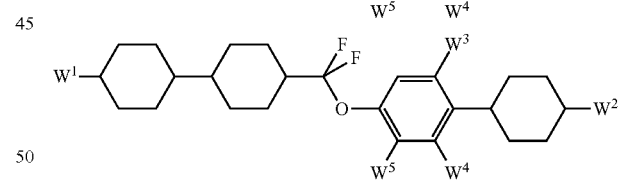

It is preferable that the liquid crystal compound to be used in the present polymerizable composition have a polymerizable functional group. Examples of the polymerizable functional group include a (meth)acryloyloxy group, a fluoroacrylic group, a chloroacrylic group, a trifluoromethylacrylic group, an oxirane ring (epoxy group), an oxetane ring, a styrene compound (styryl group), a vinyl group, a vinyl ether group, a vinyl ketone group, a maleimide group, or a phenylmaleimide group. Any commonly-used liquid crystal compounds having such a polymerizable functional group can be used. Concrete examples thereof include, but are not limited to, those described in JP-A-2005-15473, paragraphs {0172} through {0314} and compounds shown in Chem. 11 through Chem. 22 below.

[Chem. 11]
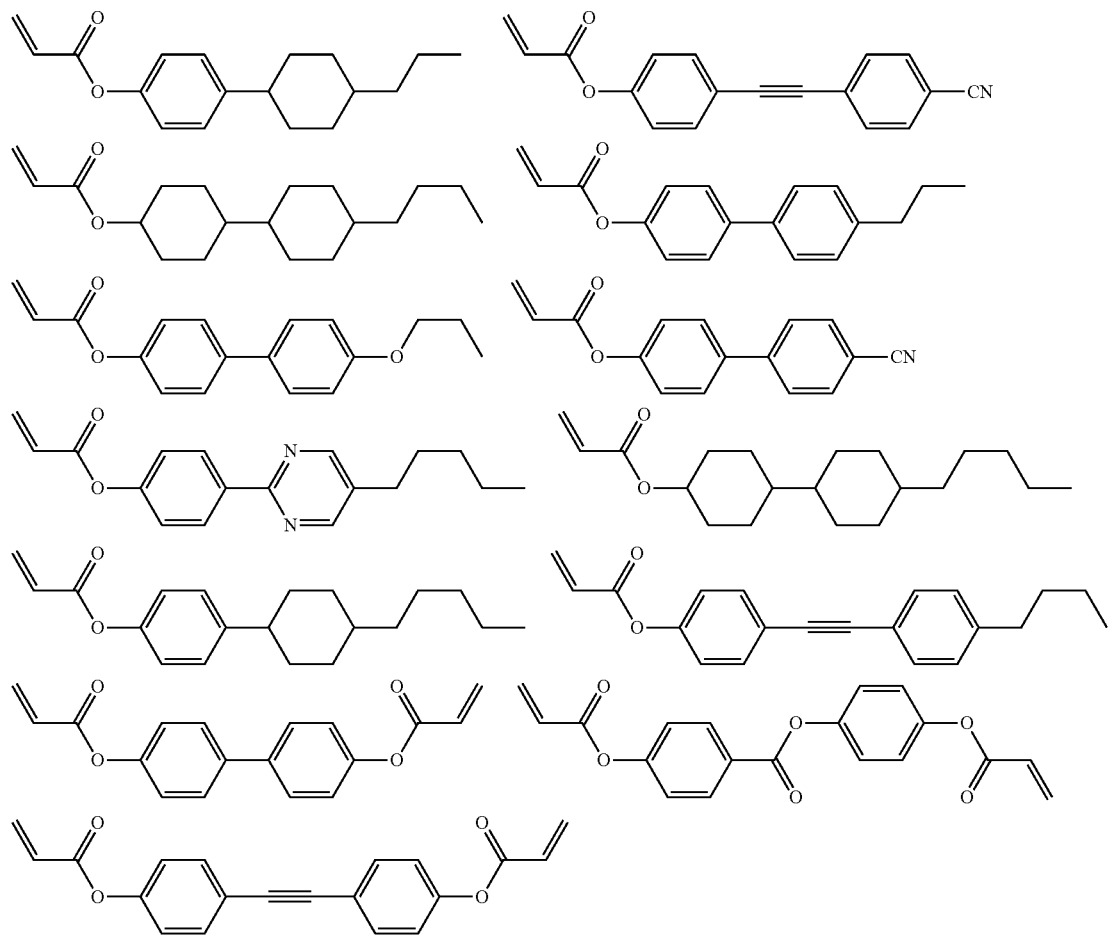
[Chem. 12]
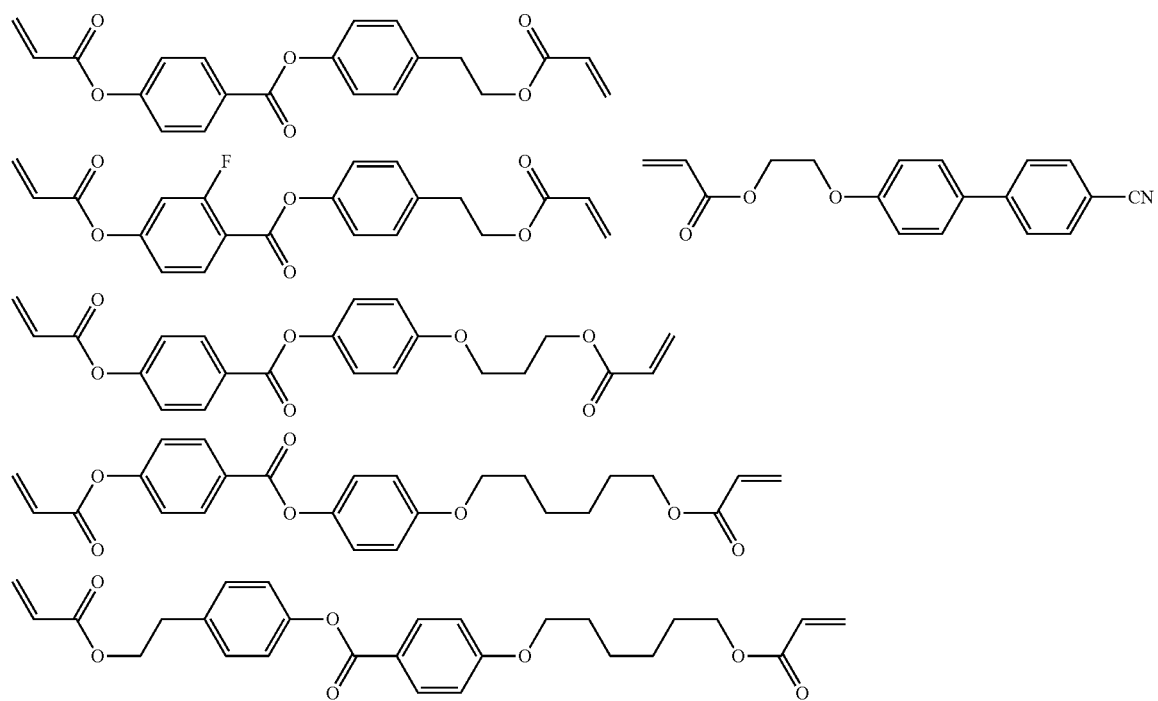

-continued
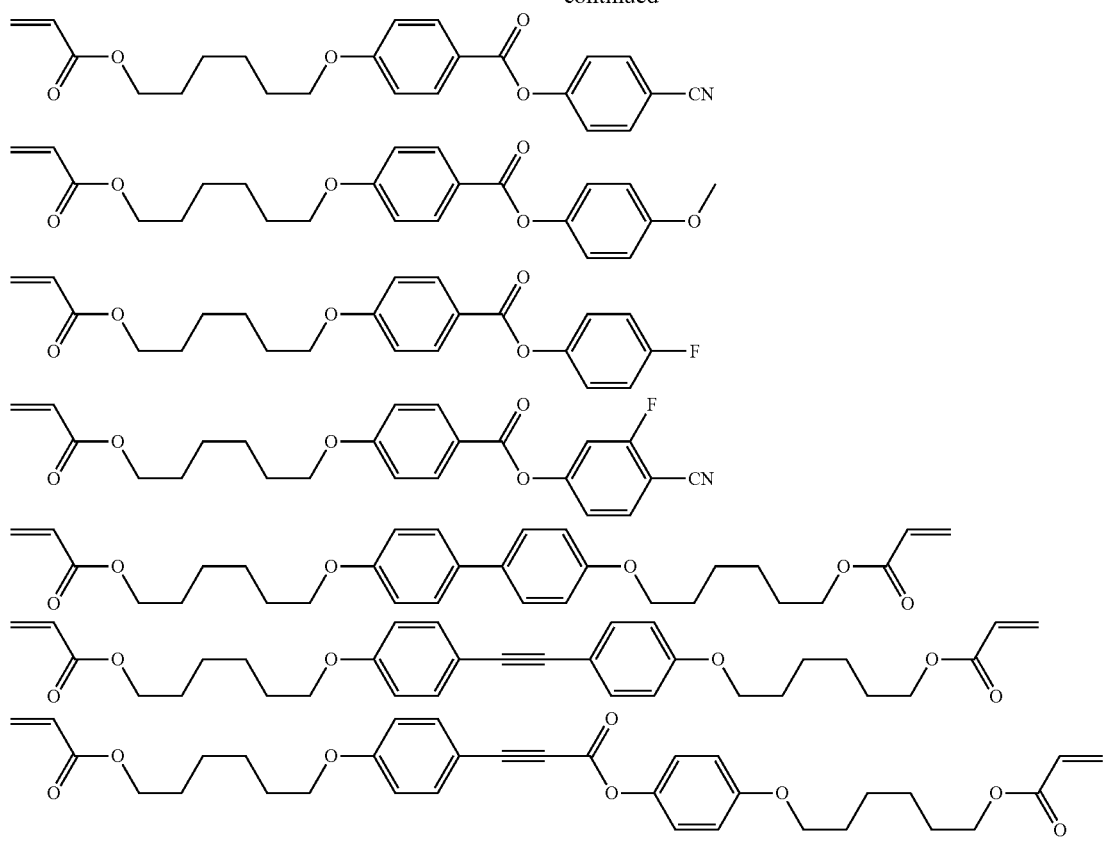
[Chem. 13]
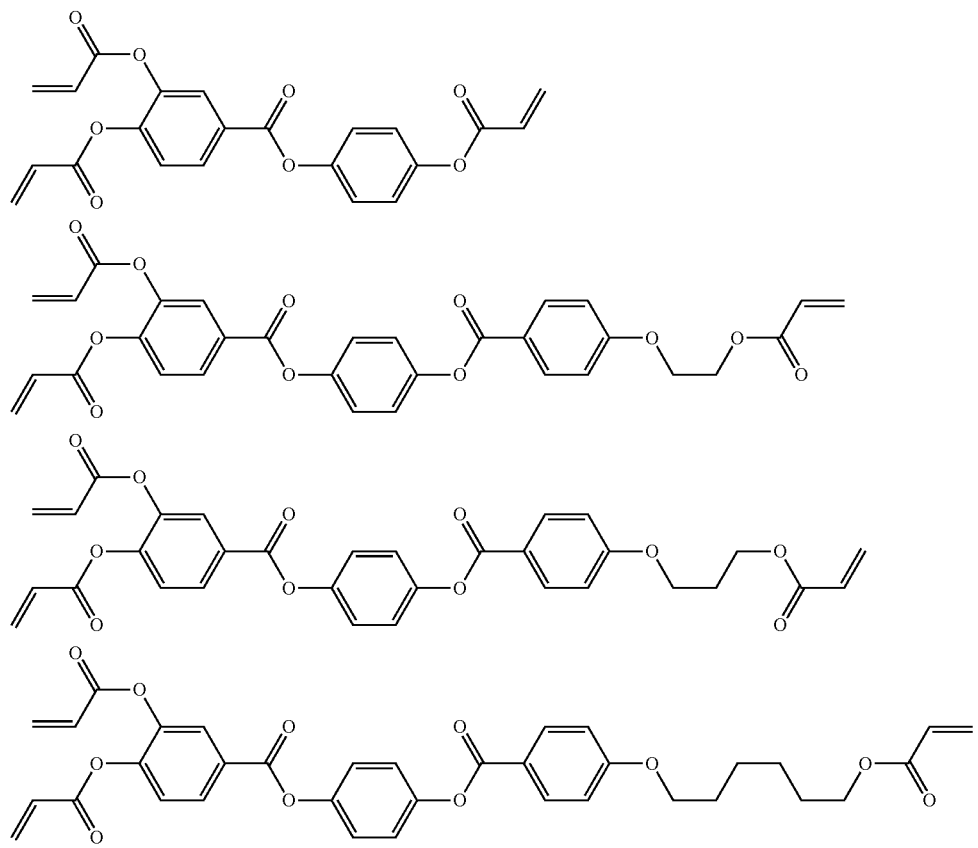

-continued
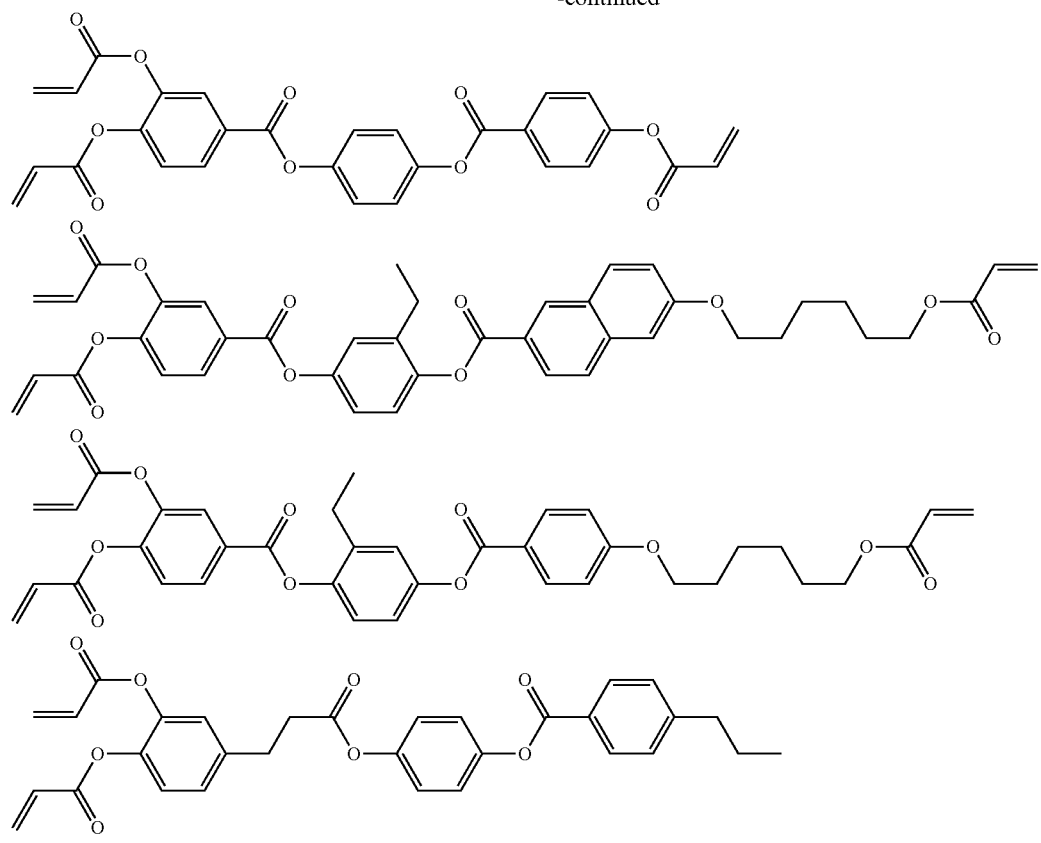
[Chem. 14]
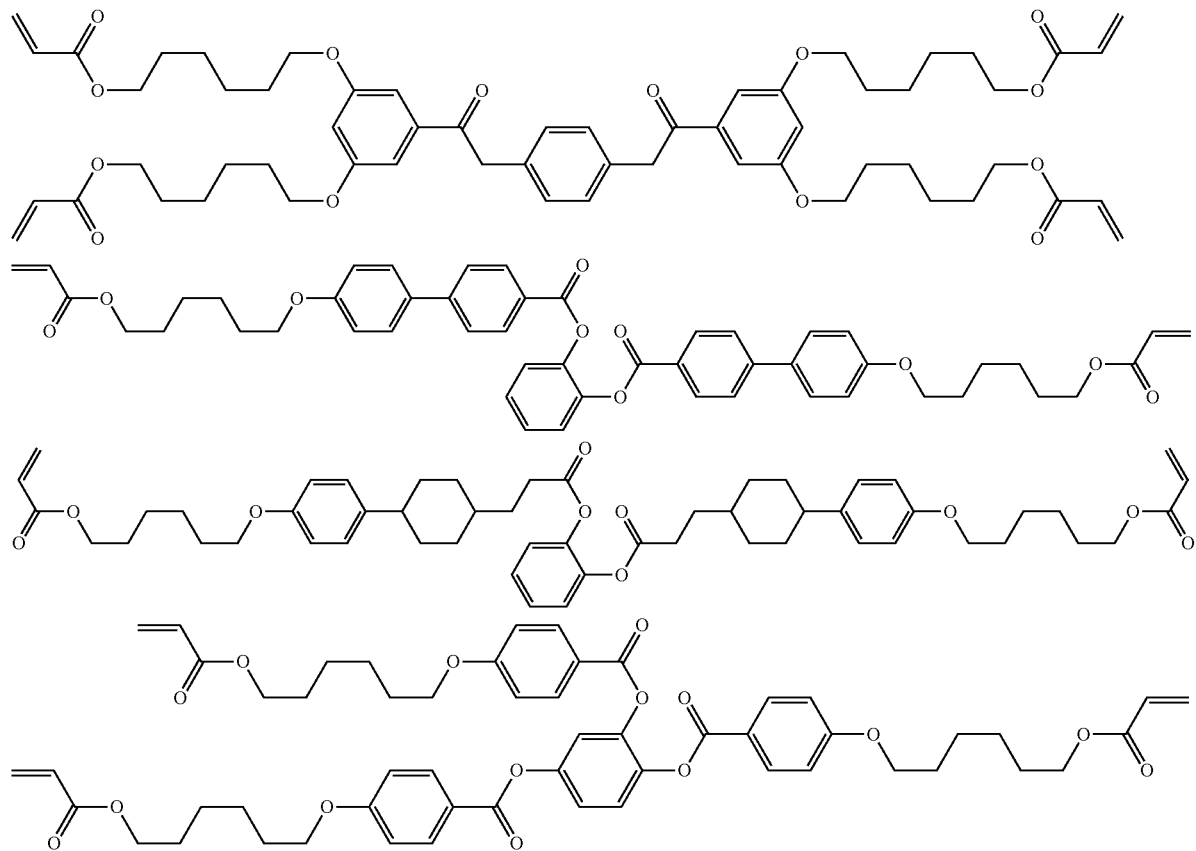

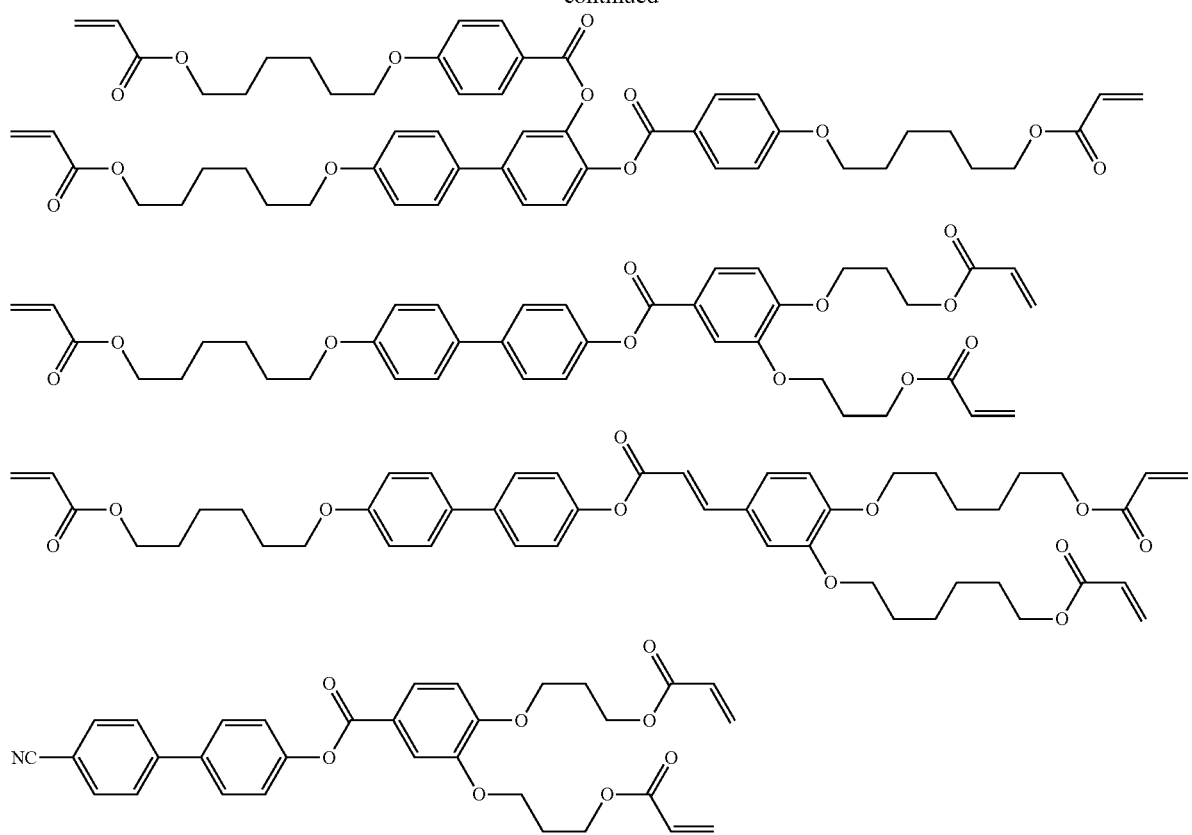
[Chem. 15]
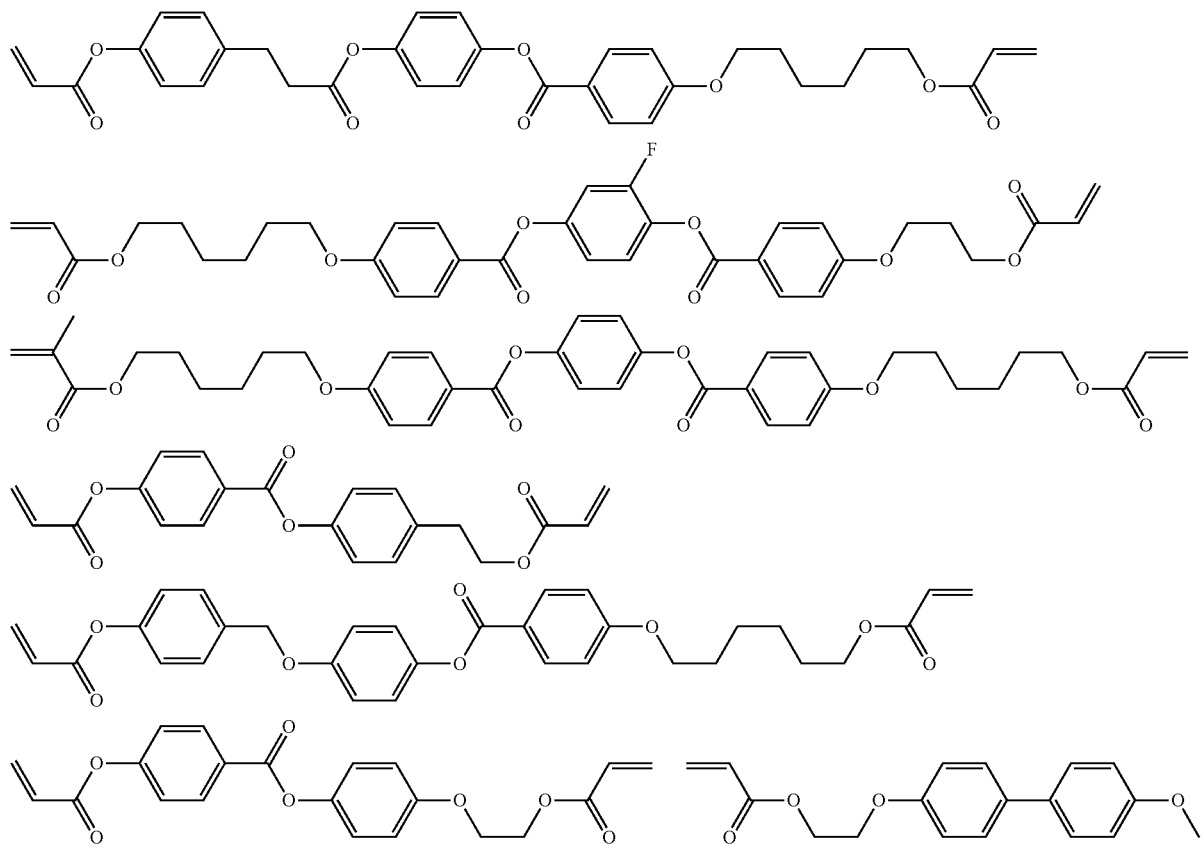

-continued
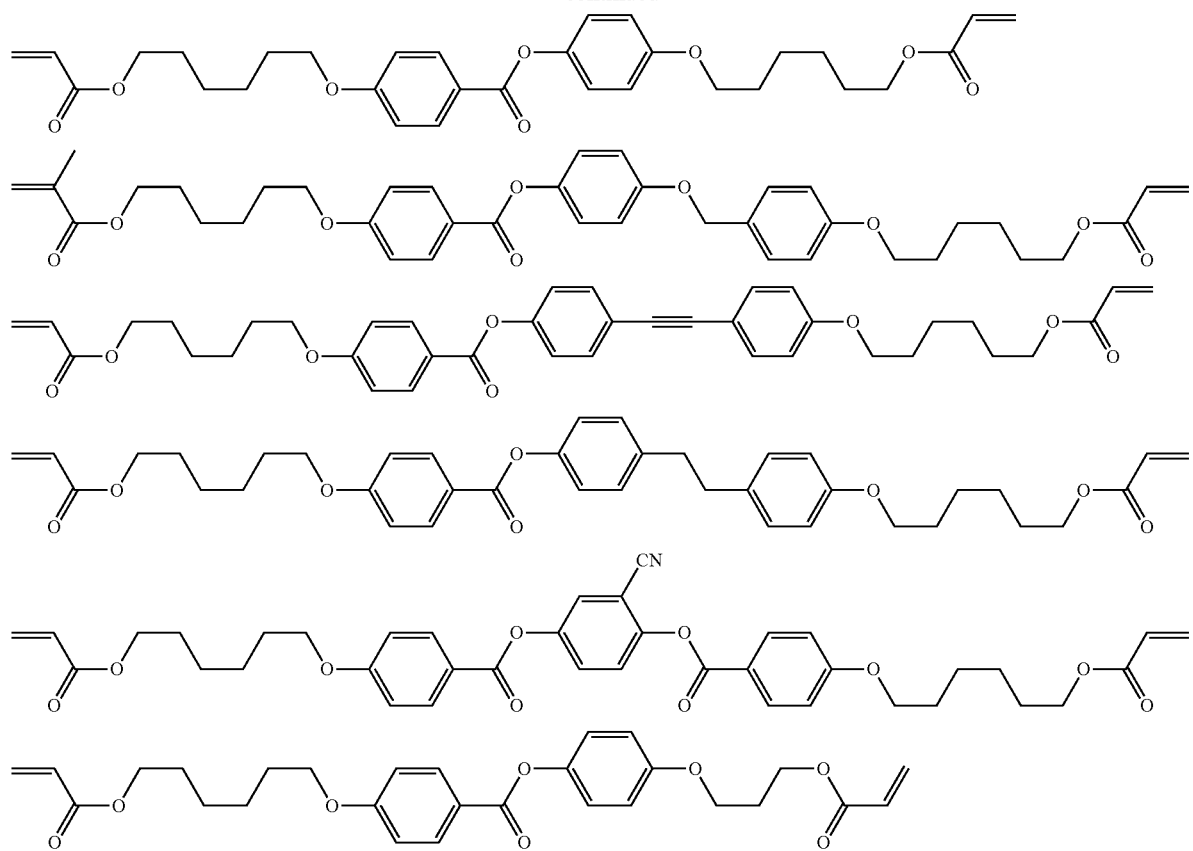
[Chem. 16]
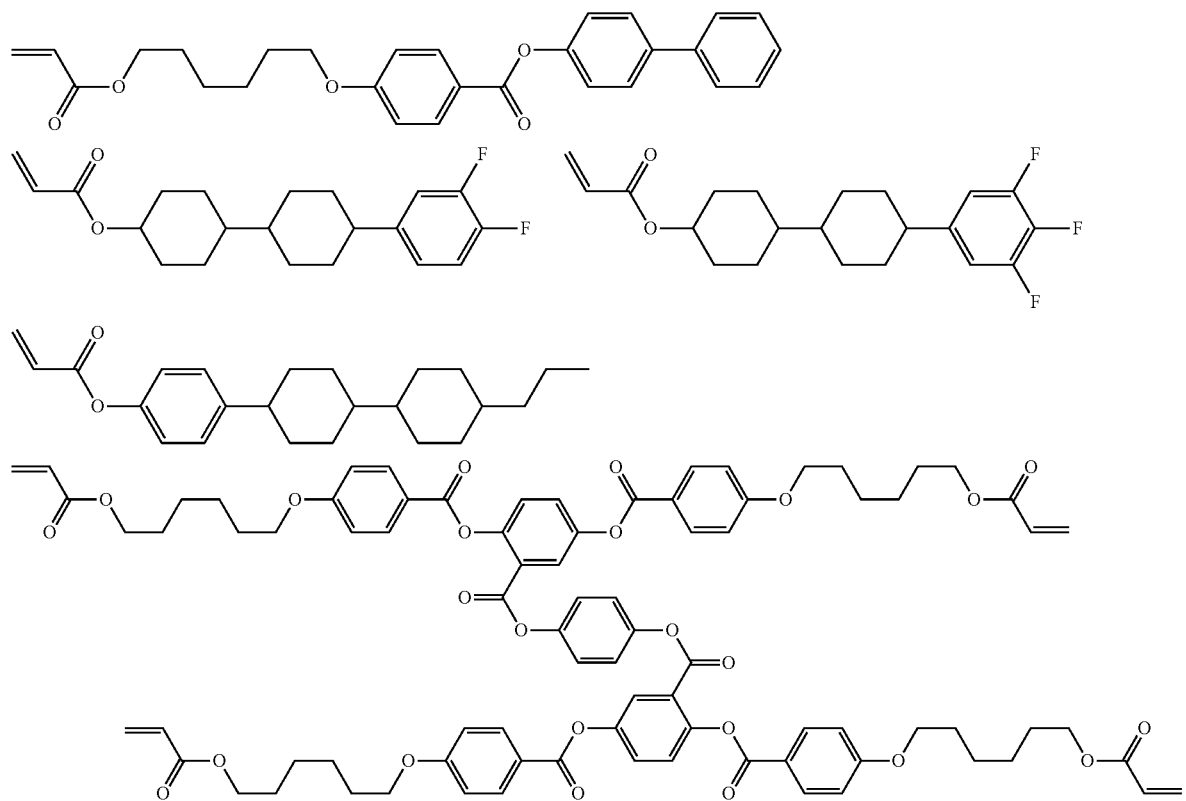

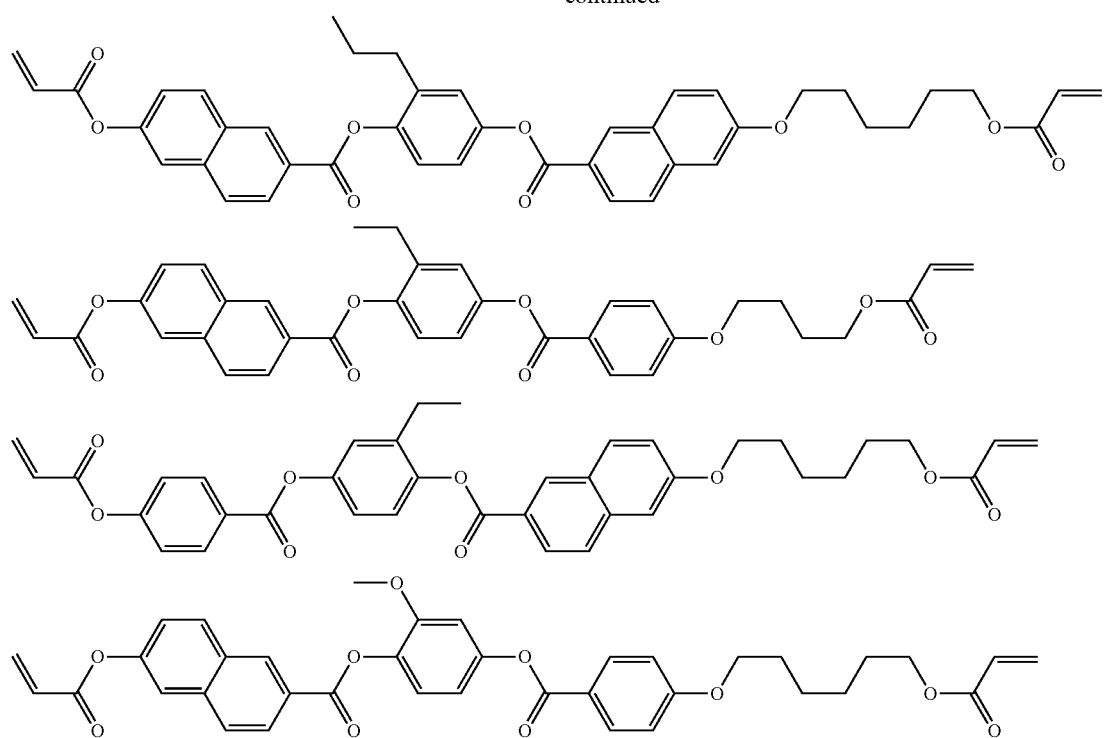
[Chem. 17]
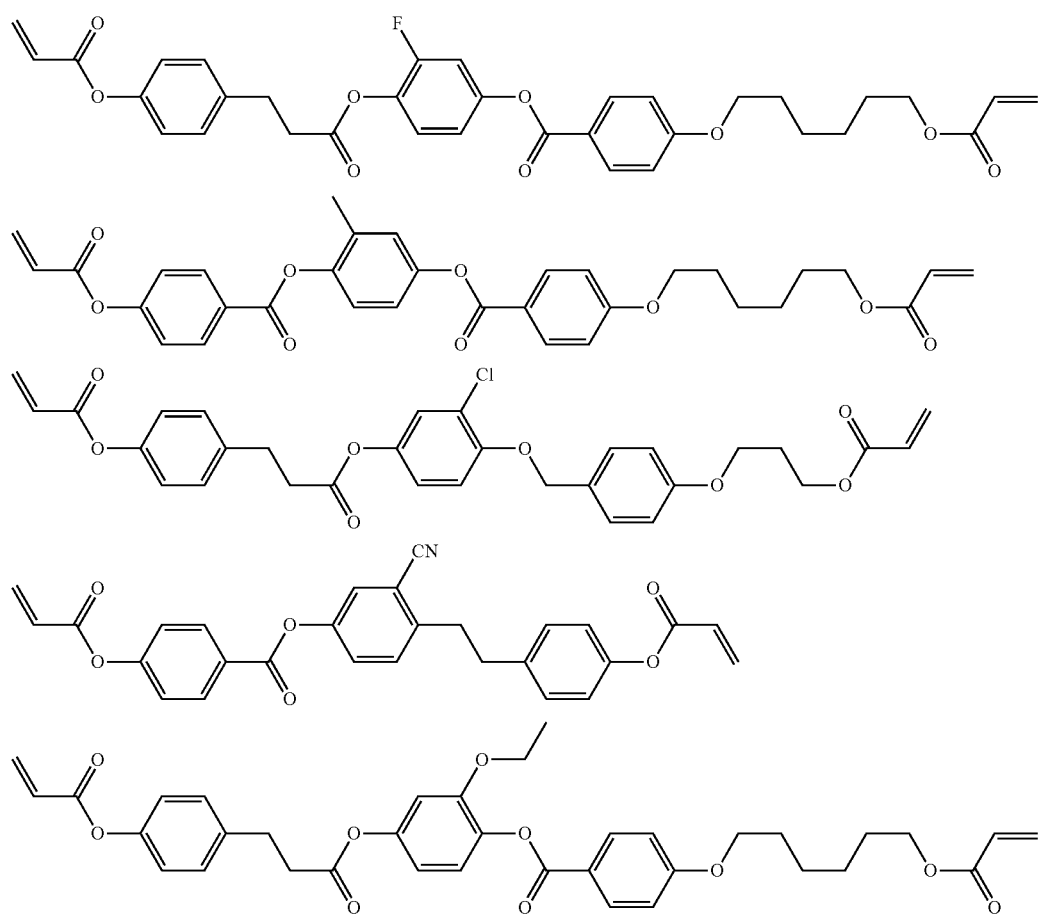

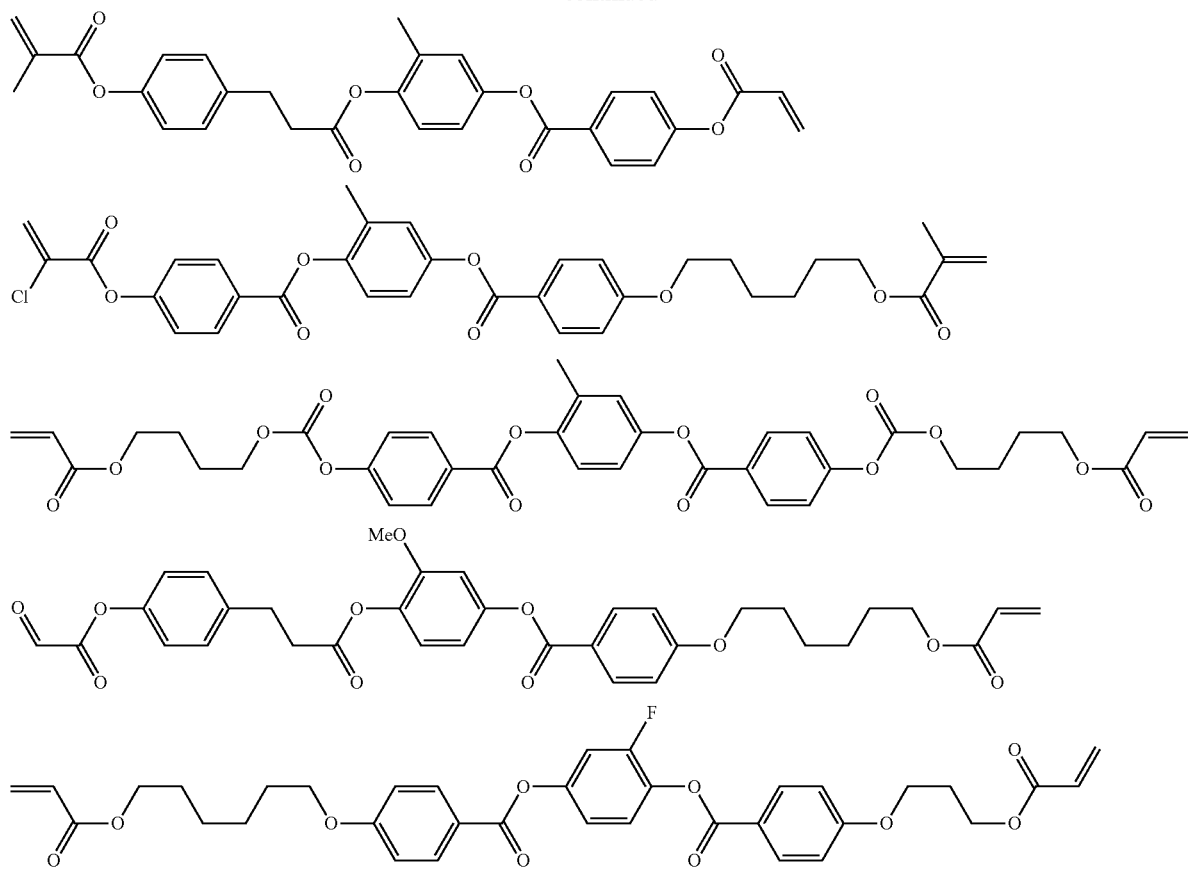
[Chem. 18]
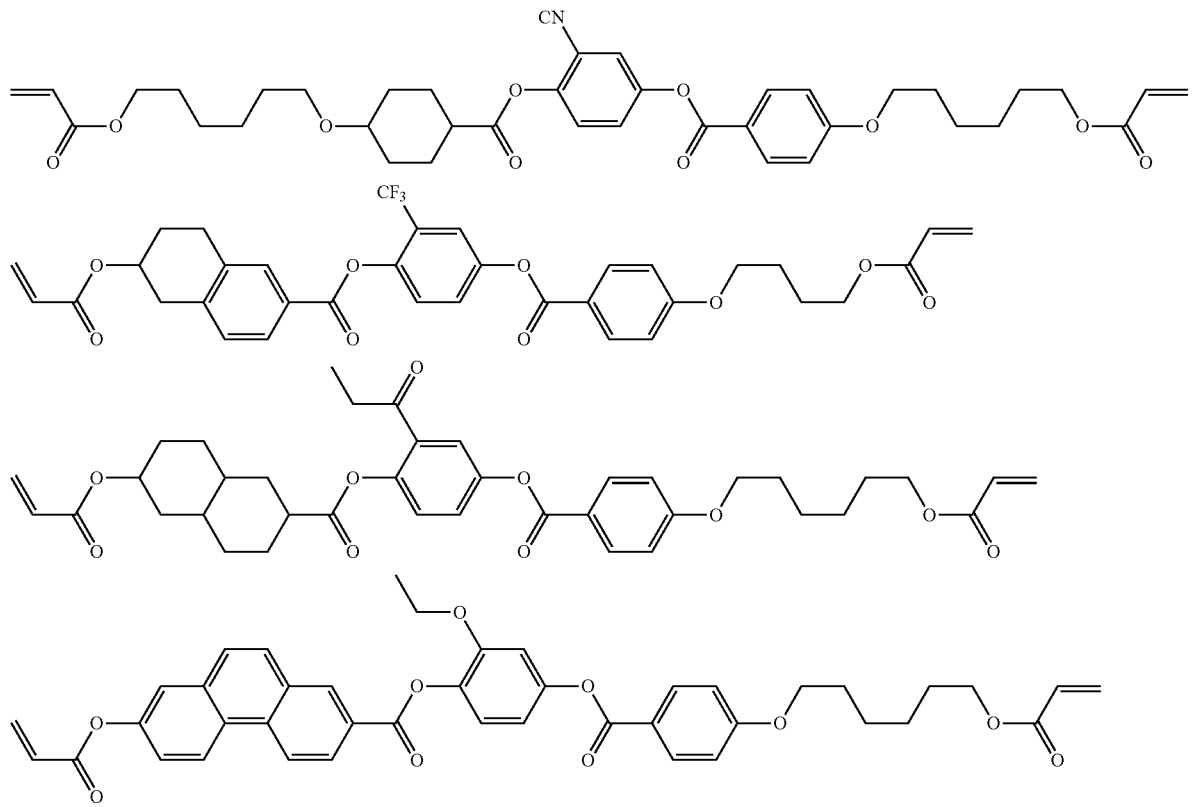

-continued
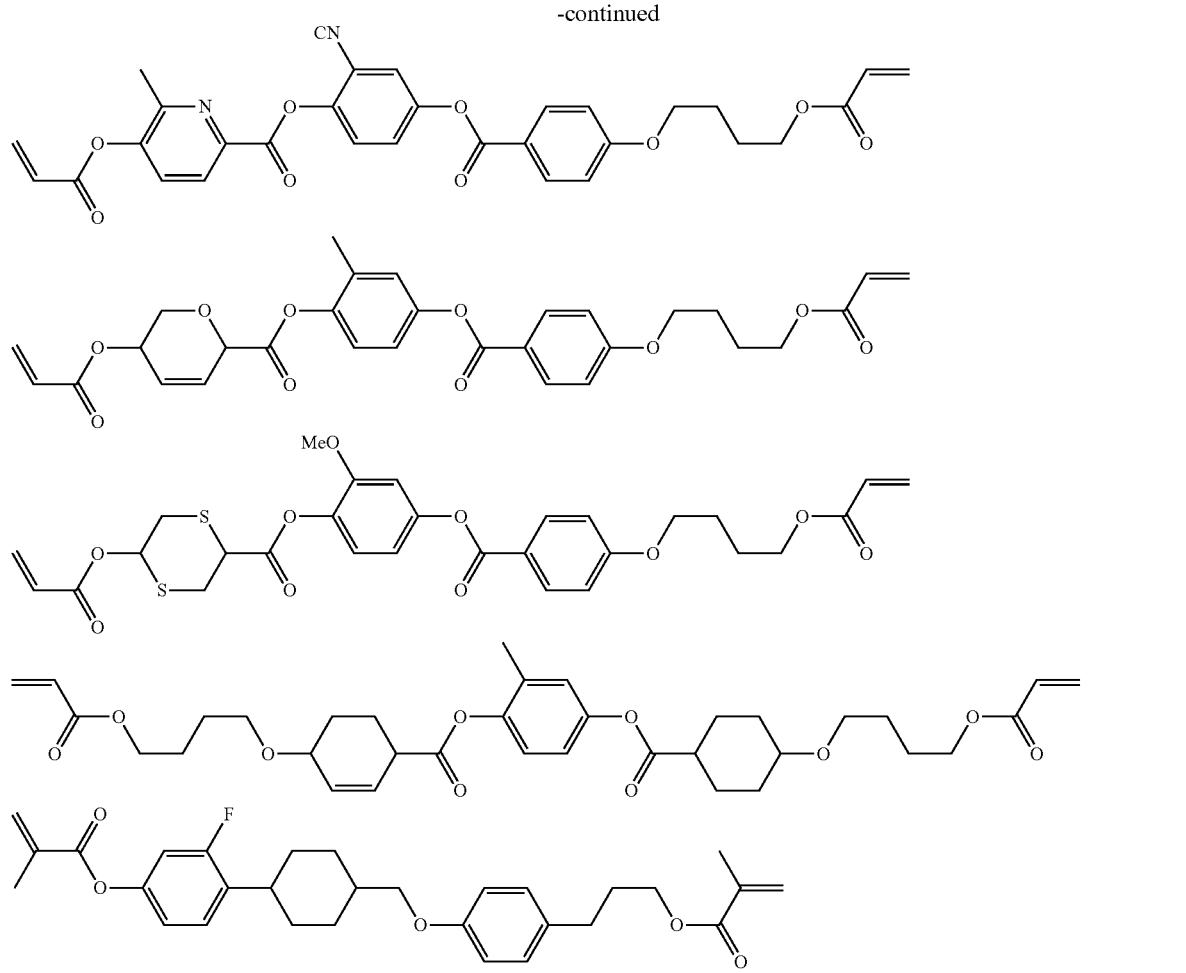
[Chem. 19]
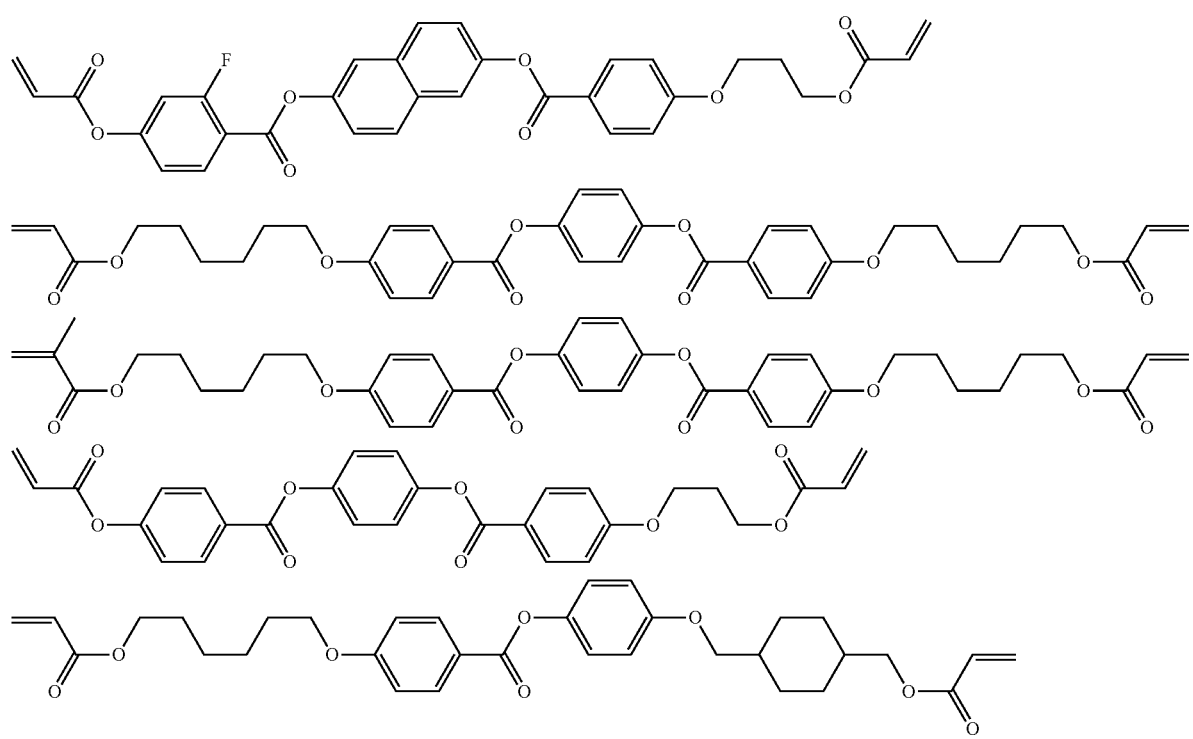

-continued
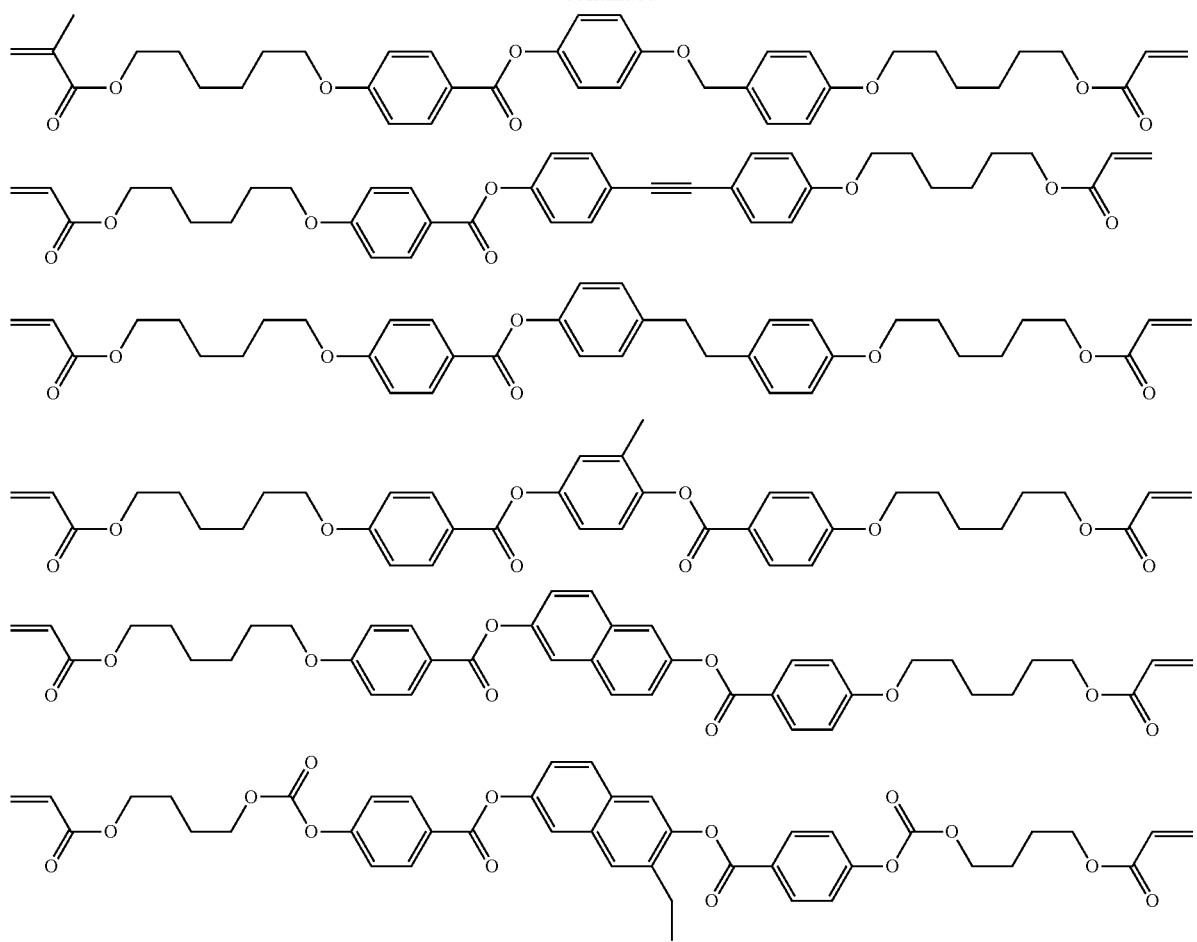
[Chem. 20]
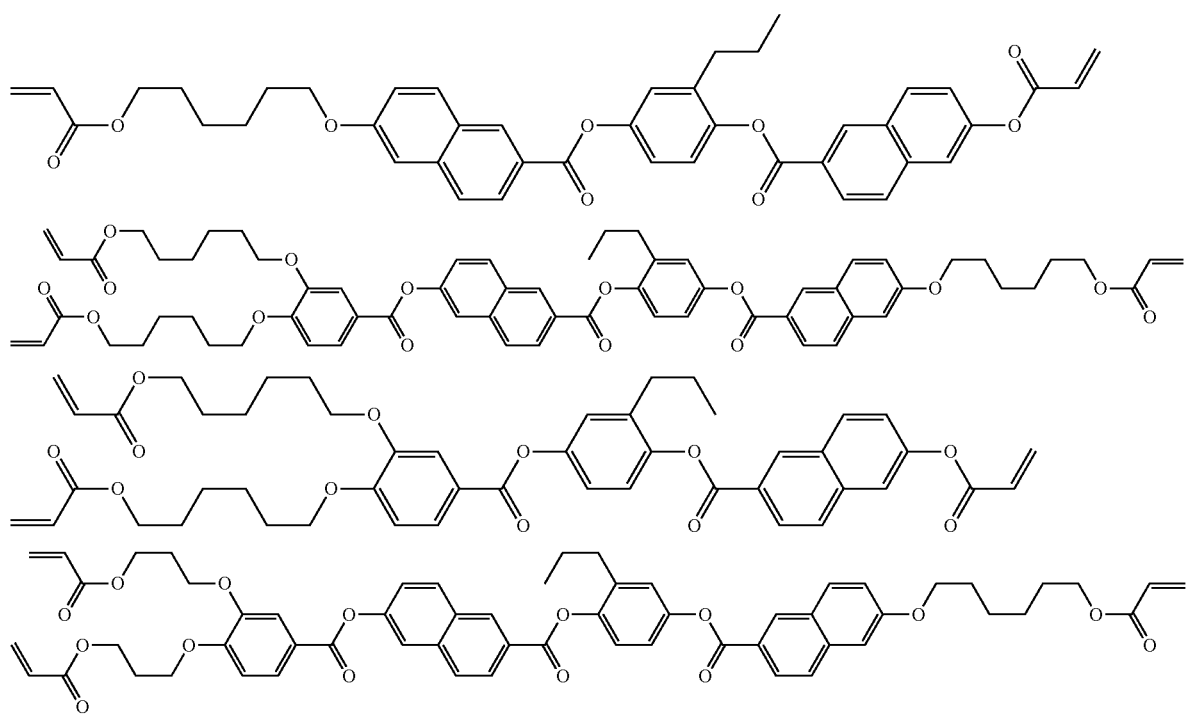

-continued
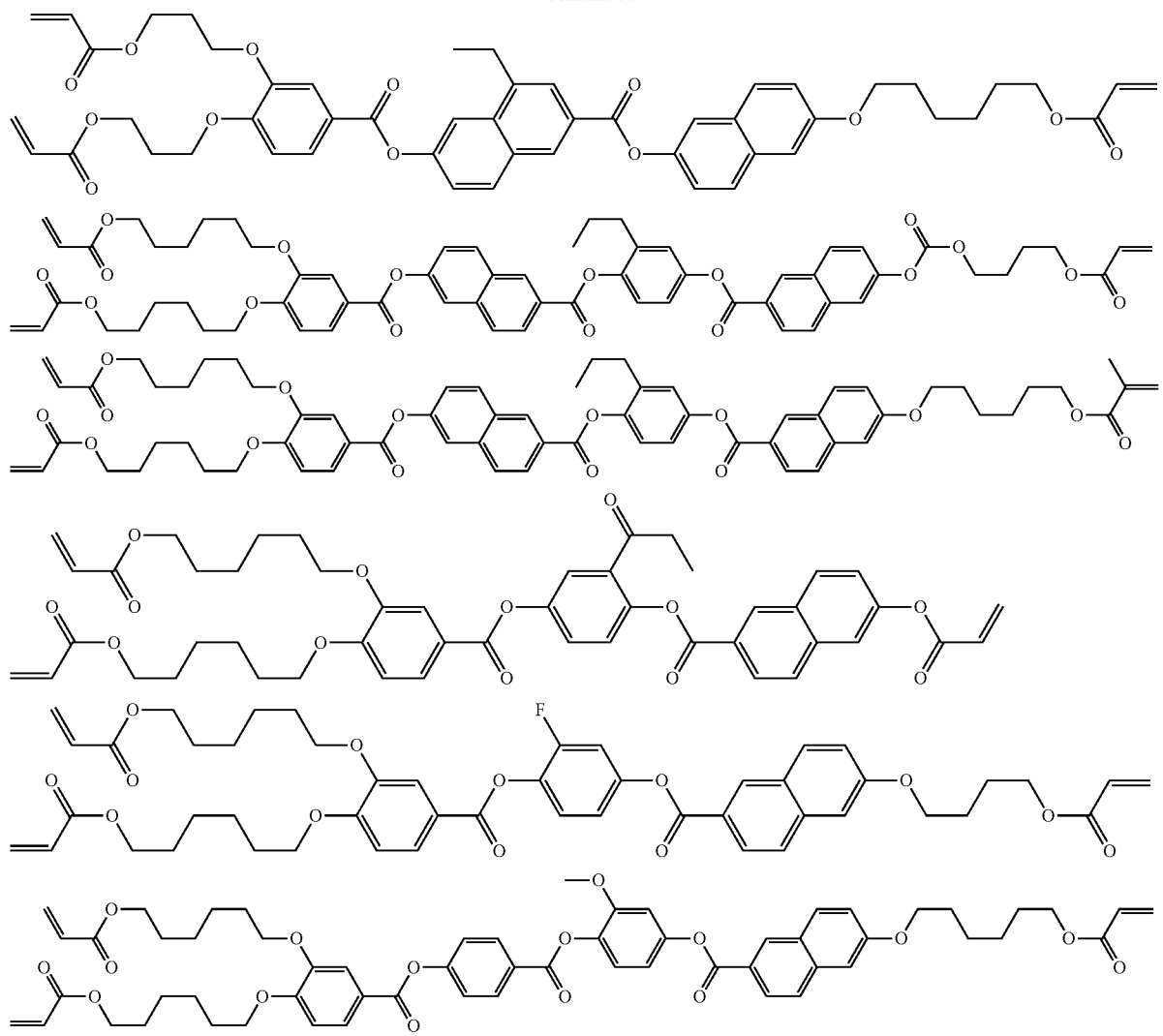
[Chem. 21]
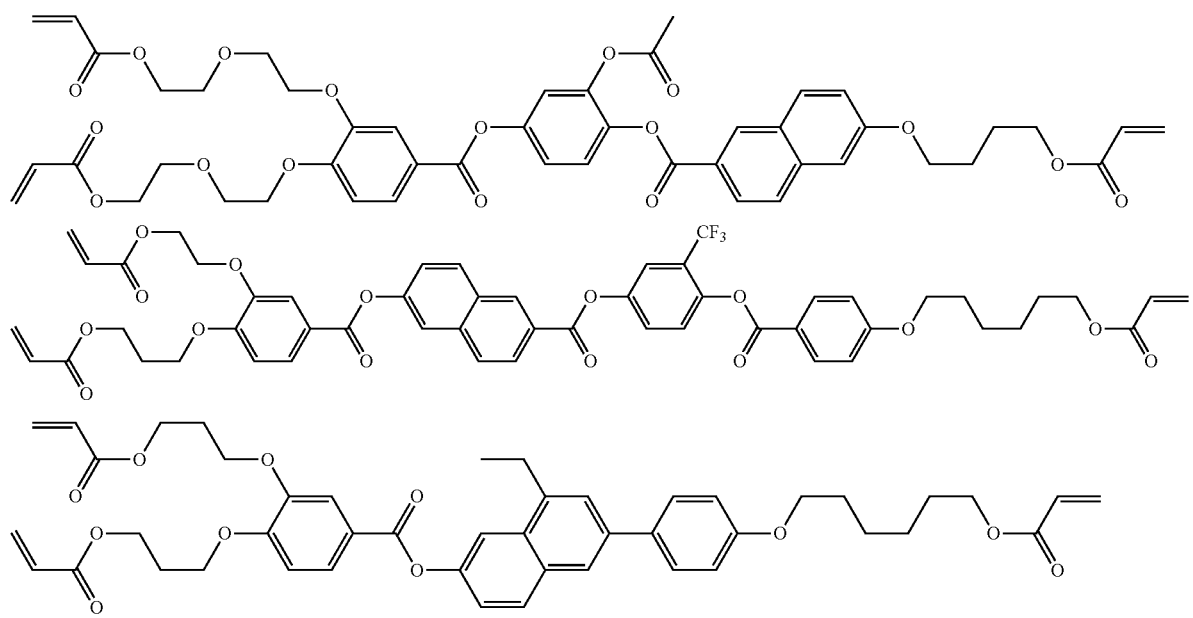

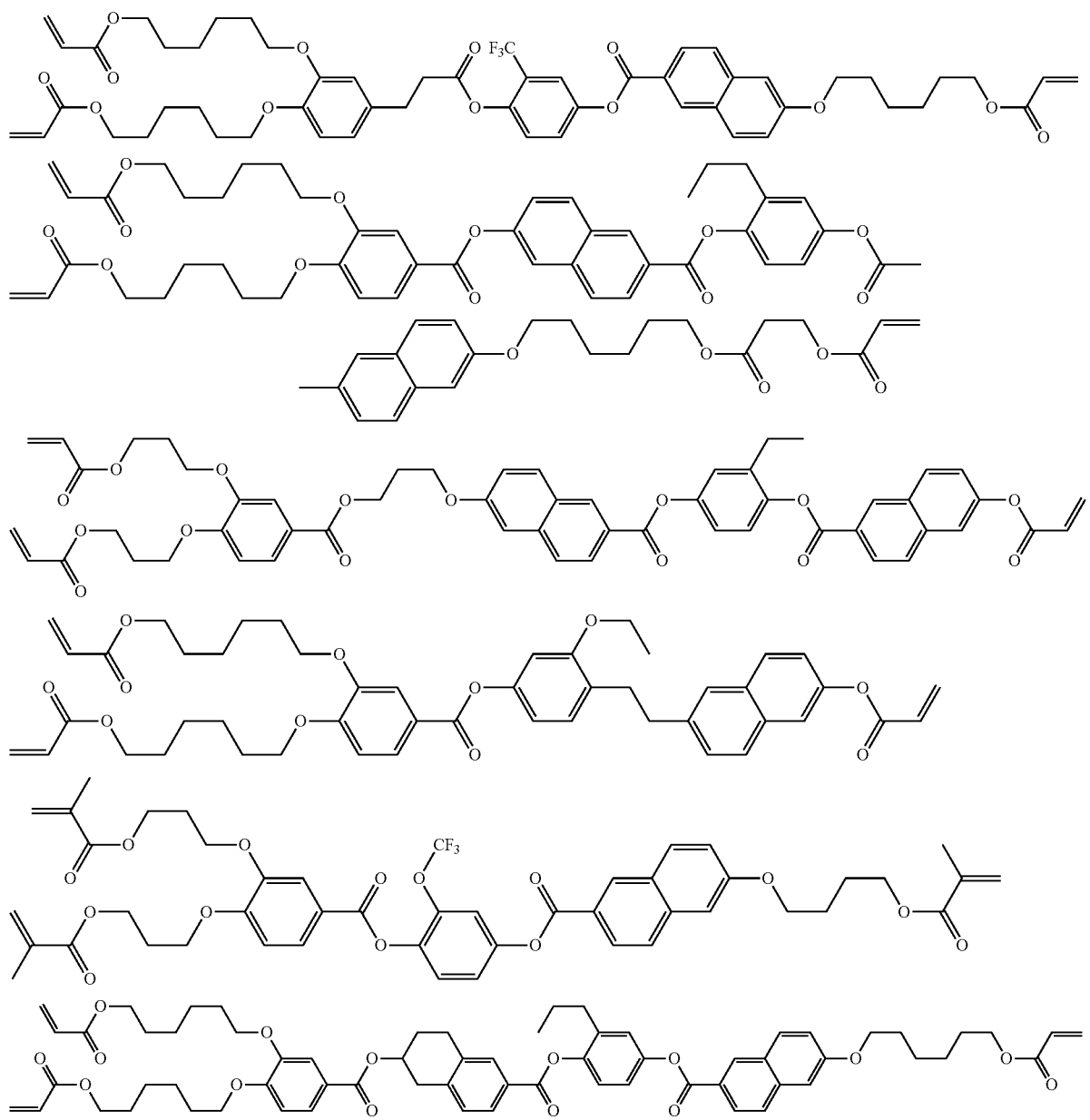
[Chem. 22]
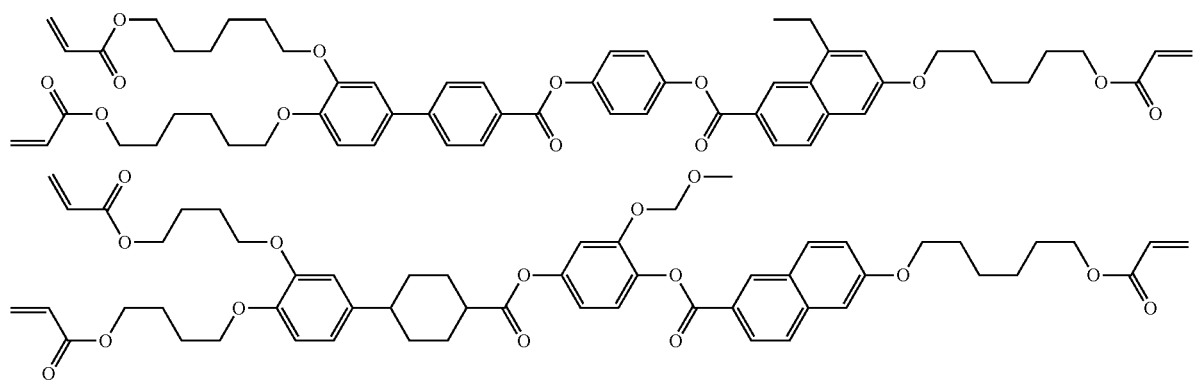

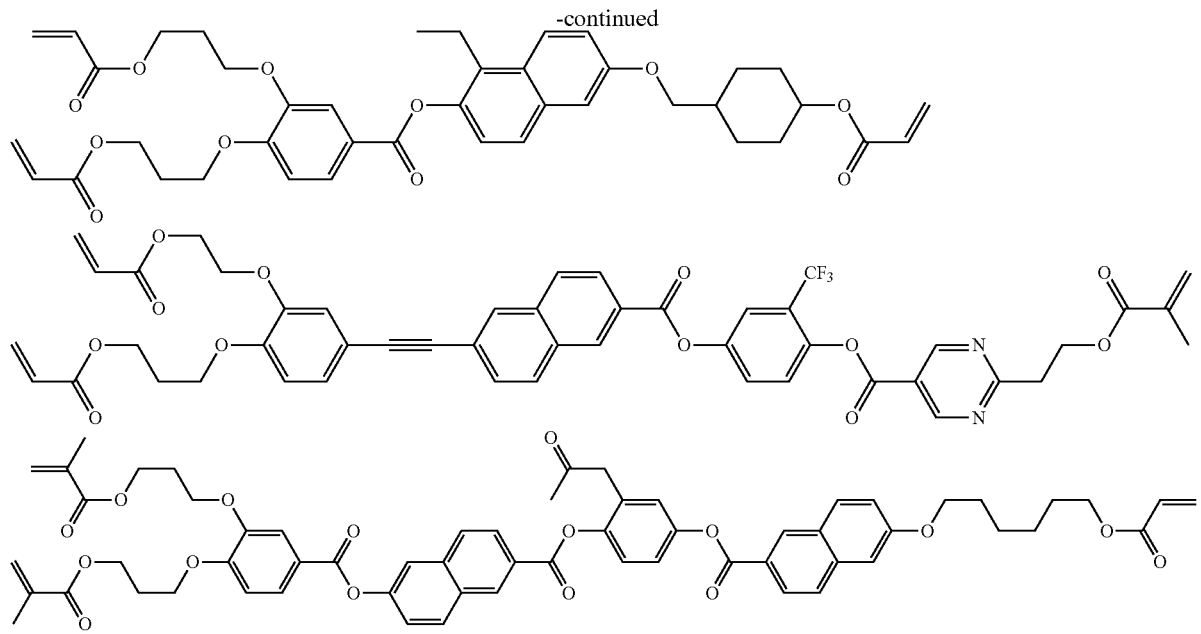

The polymerizable composition of the invention may be formulated into a solution in a solvent, together with another monomer (a compound having an ethylenically unsaturated bond) and a radical polymerization initiator where necessary.

Examples of other monomers include (meth)acrylic esters, such as methyl(meth)acrylate, ethyl(meth)acrylate, propyl(meth)acrylate, butyl(meth)acrylate, sec-butyl(meth)acrylate, tert-butyl(meth)acrylate, hexyl(meth)acrylate, 2-ethylhexyl(meth)acrylate, tetrahydrofurfuryl(meth)acrylate, glycidyl(meth)acrylate, allyl(meth)acrylate, allyloxy(meth)acrylate, cyclohexyl(meth)acrylate, benzyl(meth)acrylate, 1-phenylethyl(meth)acrylate, 2-phenylethyl(meth)acrylate, furfuryl(meth)acrylate, diphenylmethyl(meth)acrylate, naphthyl(meth)acrylate, pentachlorophenyl(meth)acrylate, 2-chloroethyl(meth)acrylate, methyl-α-chloro(meth)acrylate, phenyl-α-bromo(meth)acrylate, trifluoroethyl(meth)acrylate, tetrafluoropropyl(meth)acrylate, polyethylene glycol di(meth)acrylate, 1,4-butanediol di(meth)acrylate, 1,6-hexanediol di(meth)acrylate, trimethylolpropane tri(meth)acrylate, pentaerythritol tri(meth)acrylate, pentaerythritol tetra(meth)acrylate, dipentaerythritol penta(meth)acrylate, and dipentaerythritol hexa(meth)acrylate; diacetone acrylamide, styrene, vinyltoluene, and divinylbenzene.

In order to secure heat resistance and optical properties of the polymer prepared using the polymerizable composition of the invention, the content of the other monomer is preferably not more than 50 parts by mass, more preferably 30 parts by mass or less, per a total of 100 parts by mass of the present polymerizable optically-active imide compound and the liquid crystal compound.

Known compounds may be used as the radical polymerization initiator, and examples include: benzoin ethers such as benzoin butyl ether; benzil ketals such as benzil dimethyl ketal; α-hydroxyacetophenones such as 1-hydroxy-1-benzoylcyclohexane, 2-hydroxy-2-benzoylpropane, and 2-hydroxy-2-(4'-isopropyl)benzoylpropane; chloroacetophenones such as 4-butylbenzoyltrichloromethane and 4-phenoxybenzoyldichloromethane; α-aminoacetophenones such as 1-benzyl-1-dimethylamino-1-(4'-morpholinobenzoyl)propane, 2-morpholyl-2-(4'-methylmercapto)benzoylpropane, 9-n-butyl-3,6-bis(2'-morpholinoisobutyroyl)carbazole, and 2-methyl-1-[4-(methylthio)phenyl]-2-morpholinopropan-1-one; acylphosphine oxides such as bis (2,4,6-trimethylbenzoyl)-phenylphosphine oxide; α-dicarbonyls such as benzil and methyl benzoylformate; triazines such as p-methoxyphenyl-2,4-bis(trichloromethyl)-s-triazine, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, and 2-(p-butoxystyryl)-s-triazine; α-acyloxime esters, such as compounds disclosed in U.S. Pat. No. 6,596,445 B1, US 2001012596 A1, JP-A-2005-97141, US 2006241259 A1, US 2004170924 A1, Japanese Patent No. 3798008, and US 2007270522 A1; as well as benzoyl peroxide, 2,2'-azobisisobutyronitrile, ethylanthraquinone, 1,7-bis(9'-acridinyl)heptane, thioxanthone, 1-chloro-4-propoxythioxanthone, isopropylthioxanthone, diethylthioxanthone, benzophenone, phenylbiphenyl ketone, 4-benzoyl-4'-methyldiphenyl sulfide, 2-(p-butoxystyryl)-5-trichloromethyl-1,3,4-oxadiazole, 9-phenylacridine, 9,10-dimethylbenzphenazine, benzophenone/Michler's ketone, hexaarylbiimidazole/mercaptobenzimidazole, and thioxanthone/amine. Preferable among the above are compounds represented by the following general formula (a) or (c).

[Chem. 23]

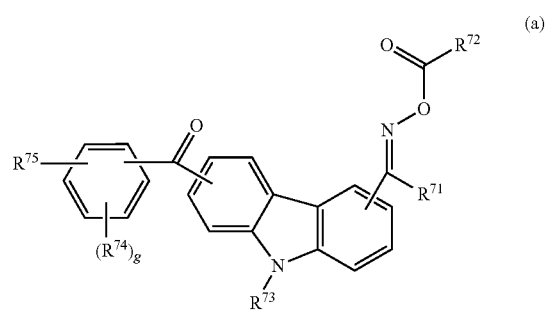

(a)

wherein, $R^{71}$, $R^{72}$, and $R^{73}$ each independently represent R, OR, COR, SR, CONRR', or CN; R and R' each independently represent an alkyl group, an aryl group, an arylalkyl group, or a heterocyclic group, each of which may be substituted by a halogen atom and/or a heterocyclic group, and the alkylene moiety of the alkyl or arylalkyl group may be interrupted by an unsaturated bond, an ether bond, a thioether bond, or an ester bond; R and R' may together form a ring; $R^{74}$ represents a halogen atom or an alkyl group; $R^{75}$ represents a hydrogen atom, a halogen atom, an alkyl group, or a substituent represented by general formula (b) below; and g represents an integer of 0 to 4, wherein when g is 2 or greater, $R^{74}$ may be different from one another.

[Chem. 24]

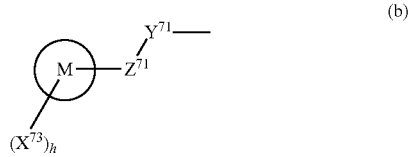

(b)

wherein, ring M represents a cycloalkane ring, an aromatic ring, or a heterocyclic ring; $X^{73}$ represents a halogen atom or an alkyl group; $Y^{71}$ represents an oxygen atom, a sulfur atom, or a selenium atom; $Z^{71}$ represents a $C_{1-5}$ alkylene group; and h represents an integer of 0 to 4, wherein when h is 2 or greater, $X^{73}$ may be different from one another.

[Chem. 25]

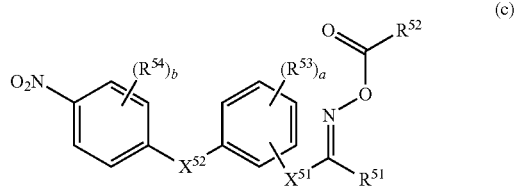

(c)

wherein, $R^{51}$ and $R^{52}$ each independently represent $R^{11}$, $OR^{11}$, $COR^{11}$, $SR^{11}$, $CONR^{12}R^{13}$, or CN; $R^{11}$, $R^{12}$, and $R^{13}$ each independently represent a hydrogen atom, a $C_{1-20}$ alkyl group, a $C_{6-30}$ aryl group, a $C_{7-30}$ arylalkyl group, or a $C_{2-20}$ heterocyclic group; a hydrogen atom in the alkyl group, the aryl group, the arylalkyl group, or the heterocyclic group may further be substituted by $OR^{21}$, $COR^{21}$, $SR^{21}$, $NR^{22}R^{23}$, $CONR^{22}R^{23}$, $-NR^{22}-OR^{23}$, $-NCOR^{22}-OCOR^{23}$, $-C(=N-OR^{21})-R^{22}$, $-C(=N-OCOR^{21})-R^{22}$, CN, a halogen atom, $-CR^{21}=CR^{22}R^{23}$, $-CO-CR^{21}=CR^{22}R^{23}$, a carboxyl group, or an epoxy group; $R^{21}$, $R^{22}$, and $R^{23}$ each independently represent a hydrogen atom, a $C_{1-20}$ alkyl group, a $C_{6-30}$ aryl group, a $C_{7-30}$ arylalkyl group, or a $C_{2-20}$ heterocyclic group; the methylene group in the alkylene moiety of the substituent represented by $R^{11}$, $R^{12}$, $R^{13}$, $R^{21}$, $R^{22}$, or $R^{23}$ may be interrupted 1 to 5 times by an unsaturated bond, an ether bond, a thioether bond, an ester bond, a thioester bond, an amide bond, or an urethane bond, the alkyl moiety in the above substituents may have a branched side chain or may be a cyclic alkyl, and the alkyl end of the above substituents may be an unsaturated bond; each pair of $R^{12}$ and $R^{13}$, as well as $R^{22}$ and $R^{23}$, may together form a ring; $R^{53}$ and $R^{54}$ each independently represent $R^{11}$, $OR^{11}$, $SR^{11}$, $COR^{11}$, $CONR^{12}R^{13}$, $NR^{12}COR^{11}$, $COR^{11}$, $COOR^{11}$, $SCOR^{11}$, $OCSR^{11}$, $COSR^{11}$, $CSOR^{11}$, CN, a halogen atom, or a hydroxyl group; a and b each independently represent 0 to 4; $X^{51}$ represents a direct bond or CO; $X^{52}$ represents an oxygen atom, a sulfur atom, a selenium atom, $CR^{31}R^{32}$, CO, $NR^{33}$, or $PR^{34}$; $R^{31}$, $R^{32}$, $R^{33}$, and $R^{34}$ each independently represent $R^H$, $OR^{11}$, $COR^{11}$, $SR^{11}$, $CONR^{12}R^{13}$, or CN; $R^{53}$ may form a ring structure by bonding with one of the carbon atoms in the adjacent benzene ring via $-X^{52}-$, or $R^{53}$ and $R^{54}$ may together form a ring; and $R^{31}$, $R^{33}$, and $R^{34}$ may each independently form a ring together with either one of the adjacent benzene rings.

It is also preferable to use the above-described radical polymerization initiator in combination with a sensitizer. Examples of usable sensitizers include thioxanthone, phenothiazine, chlorothioxanthone, xanthone, anthracene, diphenylanthracene, and rubrene. In case of adding the radical polymerization initiator and/or the sensitizer, each amount is preferably 10 parts by mass or less, more preferably 5 parts by mass or less, even more preferably 0.1 to 3 parts by mass, per a total of 100 parts by mass of the present polymerizable optically-active imide compound and the liquid crystal compound.

Examples of the solvent include benzene, toluene, xylene, mesitylene, n-butylbenzene, diethylbenzene, tetralin, methoxybenzene, 1,2-dimethoxybenzene, ethylene glycol dimethyl ether, diethylene glycol dimethyl ether, acetone, methyl ethyl ketone, methyl isobutyl ketone, cyclopentanone, cyclohexanone, ethyl acetate, methyl lactate, ethyl lactate, ethylene glycol monomethyl ether acetate, propylene glycol monomethyl ether acetate, propylene glycol monoethyl ether acetate, γ-butyrolactone, 2-pyrrolidone, N-methyl-2-pyrrolidone, dimethylformamide, chloroform, dichloromethane, carbon tetrachloride, dichloroethane, trichloroethylene, tetrachloroethylene, chlorobenzene, t-butyl alcohol, diacetone alcohol, glycerol, monoacetylene, ethylene glycol, triethylene glycol, hexylene glycol, ethylene glycol monomethyl ether, ethyl cellosolve, and butyl cellosolve. The solvent may be a single compound or a mixture. Preferable among the above are solvents having a boiling point of 60° C. to 250° C., and more preferably 60° C. to 180° C. A solvent whose boiling point is lower than 60° C. is prone to vaporize during application, resulting in unevenness in film thickness, whereas a solvent whose boiling point is higher than 250° C. tends to remain even after conducting solvent-removal steps under reduced pressure or induce thermal polymerization when treated in high temperature, resulting in degradation in orientation.

The polymerizable composition of the invention may further contain other optically-active compounds to control the selective reflection wavelength range, compatibility with liquid crystals, and the like. The amount of other optically-active compounds, if added, is preferably 0.1 to 100 parts by mass, more preferably 1 to 50 parts by mass, per a total of 100 parts by mass of the polymerizable optically-active imide compound of the invention and the liquid crystal compound. Examples of such other usable optically-active compounds include those shown in Chem. 26 below.

[Chem. 26]
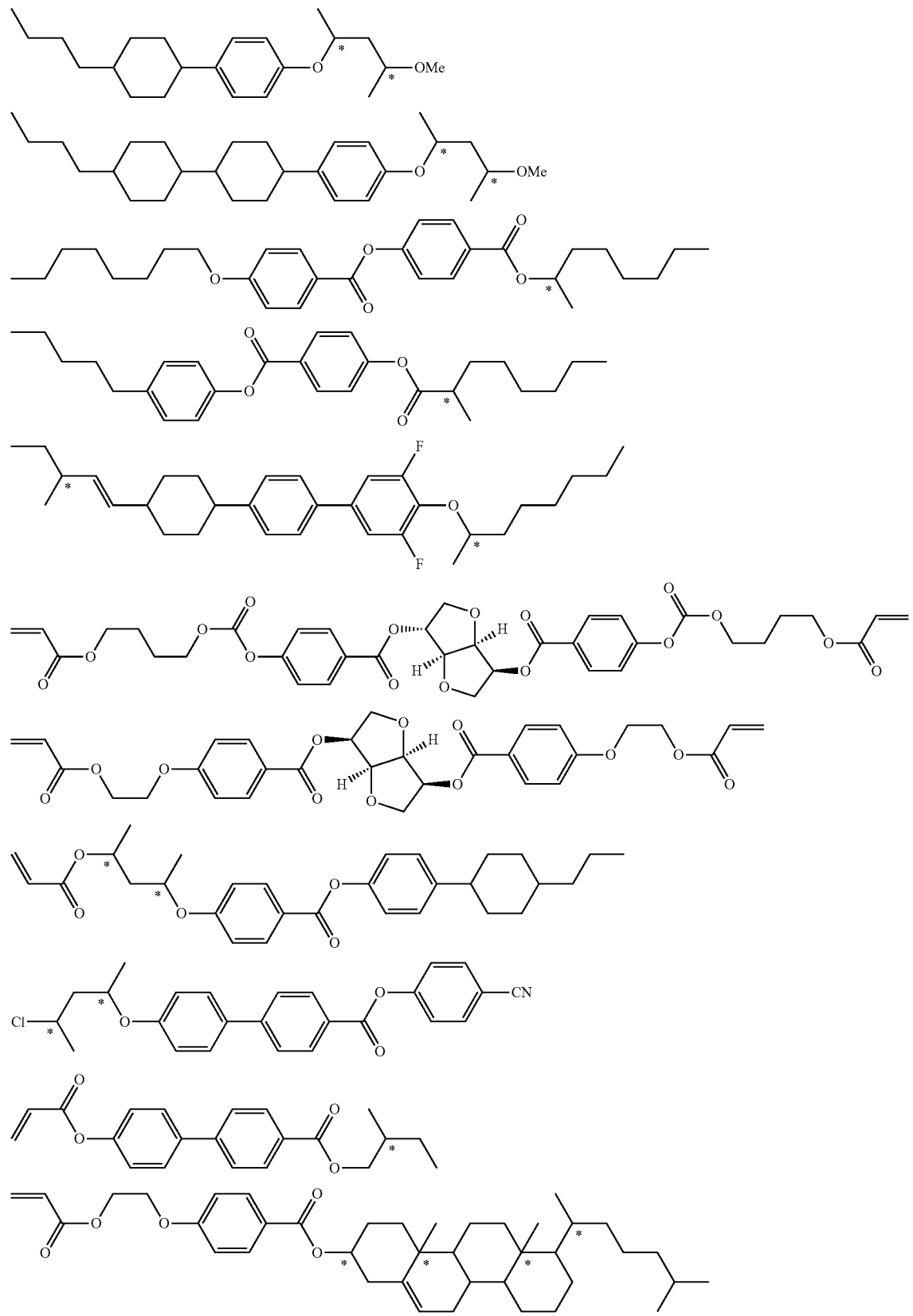

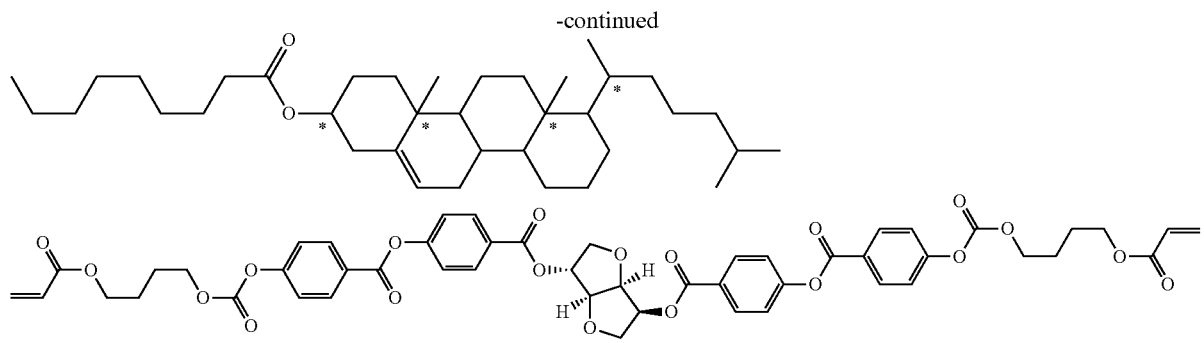

-continued

The polymerizable composition of the invention may further contain a surfactant having excluded volume effect and distributed over the interface with air. The surfactant is preferably selected from those effective in facilitating application of the polymerizable composition to a substrate or controlling the orientation of the liquid crystal phase. Such surfactants include quaternary ammonium salts, alkylamine oxides, polyamine derivatives, polyoxyethylene-polyoxypropylene condensates, polyethylene glycol and esters thereof, sodium lauryl sulfate, ammonium lauryl sulfate, amine lauryl sulfates, alkyl-substituted aromatic sulfonates, alkyl phosphates, perfluoroalkyl sulfonates, perfluoroalkyl carboxylates, perfluoroalkyl ethylene oxide adducts, and perfluoroalkyl trimethylammonium salts. The preferred amount of the surfactant to be used depends on such conditions as the kind of surfactant, the formulation of the components of the composition, etc., but preferably ranges from 0.01 to 5 parts by mass, more preferably 0.05 to 1 part by mass, per a total of 100 parts by mass of the polymerizable optically-active imide compound of the invention and the liquid crystal compound.

Other additives may further be added to the present polymerizable composition where needed. Examples of additives for adjusting the characteristics of the polymerizable composition include functional compounds, such as storage stabilizers, antioxidants, ultraviolet absorbers, infrared absorbers, fine particles of organic, inorganic or other materials, and polymers.

Storage stabilizers serve to improve storage stability of the polymerizable composition, and usable examples include hydroquinone, hydroquinone monoalkyl ethers, tert-butyl catechols, pyrogallols, thiophenols, nitro compounds, 2-naphtylamines, and 2-hydroxynaphthalenes. The amount of the storage stabilizer, if used, is preferably 1 part by mass or less, more preferably 0.5 parts by mass or less, per a total of 100 parts by mass of the polymerizable optically-active imide compound of the invention and the liquid crystal compound.

Any known antioxidant may be used without particular limitation, including hydroquinone, 2,6-di-tert-butyl-p-cresol, 2,6-di-tert-butylphenol, triphenyl phosphite, and trialkyl phosphites.

Any known UV absorber may be used without particular limitation. Usable examples include compounds imparted with UV absorbability using, e.g., salicylic ester compounds, benzophenol compounds, benzotriazole compounds, cyanoacrylate compounds, or nickel complex salt compounds.

The fine particles may be used to adjust the optical (refractive index) anisotropy (Δn) or to enhance the strength of the polymer. The fine particles may be of organic, inorganic or metallic materials, for example. The particle size is preferably 0.001 to 0.1 μm, more preferably 0.001 to 0.05 μm, to prevent coagulation. The particle size distribution is preferably narrow. The amount of the particles, if used, is preferably 0.1 to 30 parts by mass per a total of 100 parts by mass of the polymerizable optically-active imide compound of the invention and the liquid crystal compound.

Examples of the inorganic materials include ceramics, fluorophlogopite, fluorotetrasilicic mica, taeniolite, fluorovermiculite, fluorohectorite, hectorite, saponite, stevensite, montmorillonite, beidellite, kaolinite, fraipontite, $ZnO$, $TiO_2$, $CeO_2$, $Al_2O_3$, $Fe_2O_3$, $ZrO_2$, $MgF_2$, $SiO_2$, $SrCO_3$, $Ba(OH)_2$, $Ca(OH)_2$, $Ga(OH)_3$, $Al(OH)_3$, $Mg(OH)_2$, and $Zr(OH)_4$. Also, fine particles of e.g. needle crystals of calcium carbonate have optical anisotropy and may thus be used to adjust the optical anisotropy of the polymer.

Examples of the organic materials include carbon nanotubes, fullerenes, dendrimers, polyvinyl alcohol, polymethacrylates, and polyimides.

The polymer as an additive may be added to control the electric characteristics or orientation characteristics of the polymer of the invention. Examples of polymers preferably usable as an additive include polymeric compounds soluble in the above-described solvents. Examples of such polymeric compounds include polyamides, polyurethanes, polyureas, polyepoxides, polyesters, and polyester polyols.

The polymer of the present invention will now be described.

The polymer of the invention can be prepared, for example, by dissolving the polymerizable composition of the invention in a solvent to prepare a solution, applying the resulting solution to a substrate, removing the solvent from the coating film while preserving the state of orientation of the liquid crystal molecules in the polymerizable composition, and then irradiating the coating film with energy rays to cause polymerization.

It is preferable that the optically-active monomer for preparing the present polymer has high helical twisting power, can achieve the intended effects even when added in small amounts, has excellent dissolubility to other liquid crystal compounds and organic solvents, has excellent coatability, is polymerizable through irradiation with electromagnetic waves, and is colorless and does not absorb visible radiation. The present polymer also needs to have excellent transparency, mechanical strength, heat resistance, chemical resistance, and other such properties. When particularly used for optical compensation materials such as optical films etc., the polymer of the invention must exhibit such properties as selective wavelength reflection, uniform orientation, and a given change in retardation depending on the tilt angle. When used as a cut-off filter, the present polymer must also have the ability to prevent transmission of light having given wavelengths. The polymer prepared using the polymerizable optically-active imide compound of the invention exhibits selective reflection and can be oriented uniformly over the entire film surface, as will be described in further detail in later-described Examples. The present polymerizable optically-active imide compound also has high helical twisting power, and thus even a slight amount thereof will allow the selective wavelength of a liquid crystal composition, particularly a cholesteric liquid crystal composition, to be shifted toward the shorter-wavelength side. Further, the wavelength range of selectively-reflected light of the present polymerizable optically-active imide compound can be adjusted simply by changing the mesogenic structure of the compound. Furthermore, both enantiomers of the present polymerizable optically-active imide compound can be prepared easily, and polymers prepared using the respective enantiomers can be used to prepare a polymer that prevents transmission of light having given wavelengths, which is useful as a cut-off filter.

Examples of preferred substrates include, but are not limited to, plates made of glass, polyethylene terephthalate, polycarbonate, polyimide, polyamide, polymethyl methacrylate, polystyrene, polyvinyl chloride, polytetrafluoroethylene, cellulose, silicone, cycloolefin polymers, or calcite, or a reflector plate. It is also possible to suitably use a plate having a later-described polyimide orientation film or polyvinyl alcohol orientation film on the above-described substrate.

The solution containing the present polymerizable composition can be applied to the substrate by any known coating technique, including curtain coating, extrusion coating, roll coating, spin coating, dipping, bar coating, spray coating, slide coating, printing, and film casting. The thickness of the polymer film is determined as appropriate depending on usage, etc., and is preferably 0.001 to 30 µm, more preferably 0.001 to 10 µm, even more preferably 0.005 to 8 µm.

The liquid crystal molecules in the polymerizable composition of the invention can be oriented by, for example, subjecting the substrate to an orientation treatment in advance. The orientation treatment can preferably be carried out by, for example, providing a liquid crystal orientation layer, such as a polyimide orientation film or a polyvinyl alcohol orientation film, on the substrate, followed by such treatment as rubbing. Other methods include applying a magnetic or electric field to the polymerizable composition on the substrate.

The polymerizable composition of the invention can be polymerized by known processes using light, heat, or electromagnetic waves. Examples of light- or electromagnetic radiation-induced polymerization reactions include radical polymerization, anionic polymerization, cationic polymerization, coordination polymerization, and living polymerization. These polymerization reactions allow polymerization to take place easily under conditions in which the present polymerizable composition exhibits a liquid crystal phase. Cross-linking while applying a magnetic or electric field is also preferred. The liquid crystal (co)polymer formed on the substrate may be used as-is or may be stripped off from the substrate or transferred onto a different substrate as necessary.

Preferable examples of the light include ultraviolet, visible, and infrared rays. Electromagnetic radiation, such as electron beams and X rays, may also be used. Usually, ultraviolet or visible rays are preferred. Preferably, the wavelength range is from 150 to 500 nm, more preferably from 250 to 450 nm, even more preferably 300 to 400 nm. Examples of light sources include low pressure mercury lamps (e.g., bactericidal lamps, fluorescent chemical lamps, and black lights), high pressure discharge lamps (e.g., high pressure mercury lamps and metal halide lamps), and short arc discharge lamps (e.g., ultrahigh pressure mercury lamps, xenon lamps, and mercury xenon lamps); among these, ultrahigh pressure mercury lamps are used preferably. The polymerizable composition may be irradiated with rays of light as emitted from a light source or with rays of light of a specific wavelength (or within a specific wavelength range) selected through a filter. Preferably, the irradiation energy density is 2 to 5000 mJ/cm$^2$, more preferably 10 to 3000 mJ/cm$^2$, even more preferably 100 to 2000 mJ/cm$^2$. Preferably, the intensity of illumination is 0.1 to 5000 mW/cm$^2$, more preferably 1 to 2000 mW/cm$^2$. The temperature during irradiation may be determined so that the polymerizable composition will exhibit a liquid crystal phase and is preferably 100° C. or lower. Temperatures higher than 100° C. may give rise to thermal polymerization, which may result in poor orientation.

For example, the polymer of the invention can be used for optical films, such as retardation films (e.g., half-wave plates, quarter-wave plates, or negative C-plates), polarizers, dichroic polarizing plates, antireflective films, selective reflection films, viewing angle compensation films, and luminance improving films. The present polymer also finds use in orientation-controlling materials such as liquid crystal orientation films, optical lenses such as liquid crystal lenses or microlenses, polymer dispersed liquid crystal (PDLC) displays, electronic paper, color filters, wavelength cut-off filters, holographic elements, nonlinear optical elements, optical memories, information recording materials such as anti-counterfeit agents, adhesives, cosmetic products, and ornamental products.

EXAMPLES

The present invention will now be described in further detail according to Examples thereof. The invention, however, is not to be limited thereto.

Examples 1-1 to 1-5 describe examples of producing Compounds Nos. 1 to 5 as examples of the polymerizable optically-active imide compounds of the invention. Examples 2-1 to 2-5 describe examples of preparing polymerizable compositions and polymers according to the invention. Evaluation Examples 1 to 3 describe examples of evaluating the polymers of the invention through selective reflection measurement, orientation examination, and retardation measurement.

Example 1-1

Production of Compound No. 1

[Chem. 27]

Compound No. 1

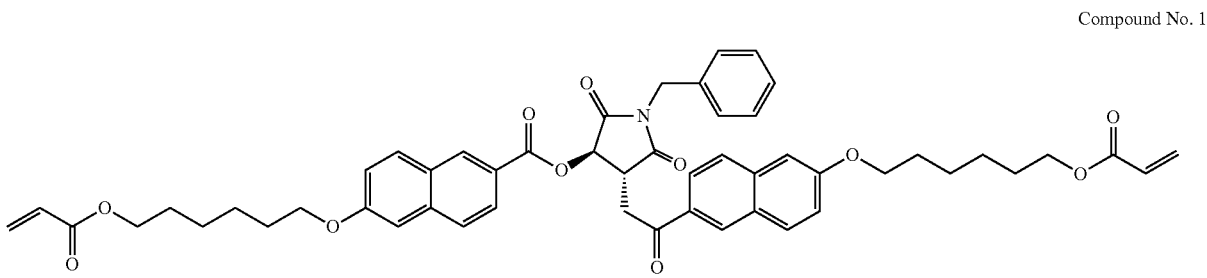

To 15 mL of acetonitrile was dissolved 1.94 g (10.2 mmol) of p-toluenesulfonyl chloride, and the solution was cooled with ice. To the cooled solution was added a suspension, in 15 mL of acetonitrile, of 2.91 g (8.50 mmol) of 2-(6-acryloyloxyhexyloxy)naphthalene-6-carboxylic acid and 2.09 g (25.5 mmol) of N-methylimidazole, and the mixture was stirred at room temperature for 1 hour. Then, while cooling the mixture with ice, a mixed solution of 0.94 g (4.25 mmol) of (+)-N-benzyl-L-tartarimide in 10 mL of acetonitrile and 15 mL of tetrahydrofuran was added to the mixture. The mixture was stirred for 30 minutes while cooling with ice, and was then stirred at room temperature for 1.8 hours. To the resulting reaction solution was added 2.62 g of concentrated hydrochloric acid, and then the solvent was removed by evaporation under reduced pressure. The residue was refined twice through silica gel column chromatography (developing solvent used first: 1:1 (v/v) of ethyl acetate:hexane; developing solvent used second time: 1:3 (v/v) of ethyl acetate:hexane), to yield 3.15 g of a colorless oily substance (yield: 85.1%). Various analyses showed that the colorless oily substance was the target Compound No. 1.

Example 1-2

Production of Compound No. 2

[Chem. 28]

Compound No. 2

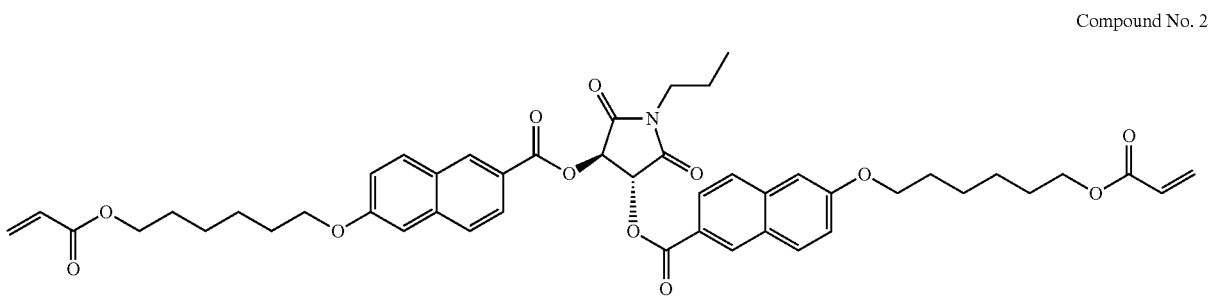

To 14 mL of acetonitrile was dissolved 2.29 g (12.0 mmol) of p-toluenesulfonyl chloride, and the solution was cooled with ice. To the cooled solution was added a suspension, in 30 mL of acetonitrile, of 3.42 g (10.0 mmol) of 2-(6-acryloyloxyhexyloxy)naphthalene-6-carboxylic acid and 2.46 g (30.0 mmol) of N-methylimidazole, and the mixture was stirred at room temperature for 1 hour. Then, while cooling the mixture with ice, a solution of 0.87 g (5.00 mmol) of (+)-N-propyl-L-tartarimide in 10 mL of tetrahydrofuran was added to the mixture. The mixture was stirred for 2.5 hours while cooling with ice, and then the solvent was removed by evaporation under reduced pressure. The residue was refined through silica gel column chromatography (developing solvent: 1:3 (v/v) of ethyl acetate:hexane), to yield 3.06 g of a colorless oily substance (yield: 74.4%). Various analyses showed that the colorless oily substance was the target Compound No. 2.

Example 1-3

Production of Compound No. 3

[Chem. 29]

Compound No. 3

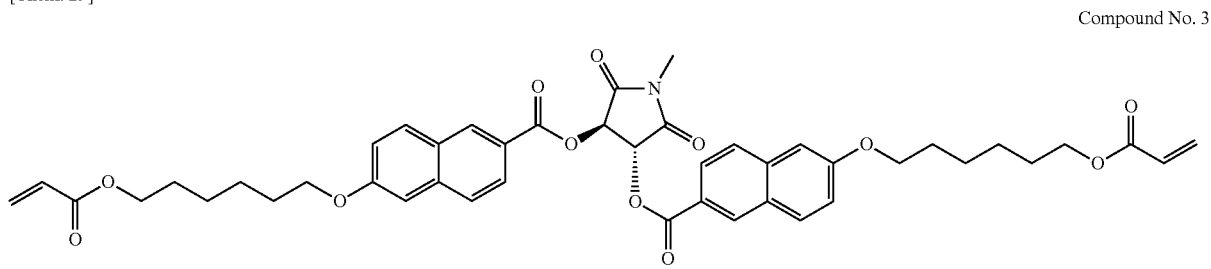

The same procedure as in Example 1-2 was followed, except that (+)-N-propyl-L-tartarimide was changed to 0.73 g (5.00 mmol) of (+)-N-methyl-L-tartarimide, to yield 3.32 g of a colorless oily substance (yield: 83.6%). Various analyses showed that the colorless oily substance was the target Compound No. 3.

Example 1-4

Production of Compound No. 4

[Chem. 30]

Compound No. 4

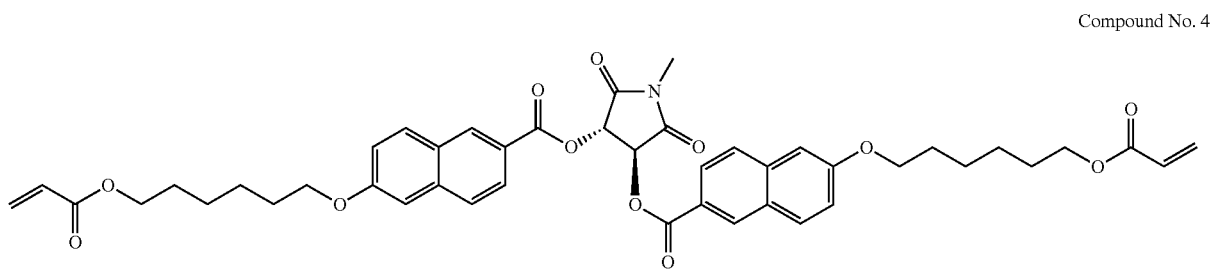

The same procedure as in Example 1-2 was followed, except that (+)-N-propyl-L-tartarimide was changed to 0.73 g (5.00 mmol) of (−)-N-methyl-D-tartarimide, to yield 3.63 g of a colorless oily substance (yield: 91.4%). Various analyses showed that the colorless oily substance was the target Compound No. 4.

Example 1-5

Production of Compound No. 5

[Chem. 31]

Compound No. 5

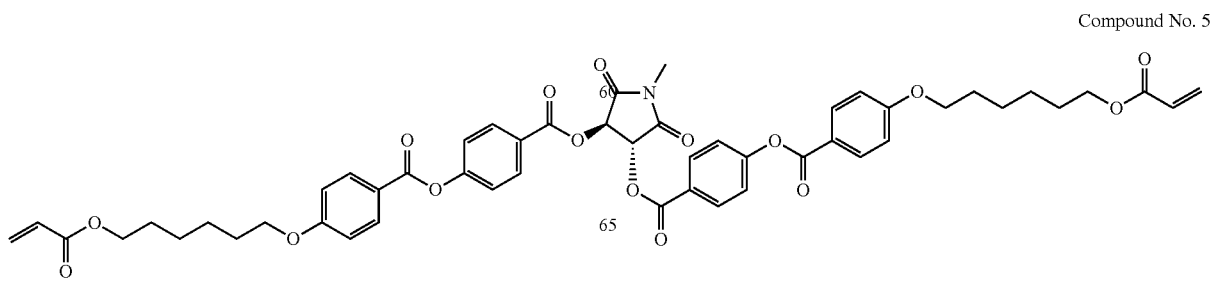

To 14 mL of acetonitrile was dissolved 2.31 g (12.1 mmol) of p-toluenesulfonyl chloride, and the solution was cooled with ice. To the cooled solution was added a suspension, in 31 mL of acetonitrile, of 2.95 g (10.1 mmol) of 4-[4-(6-acryloyloxyhexyloxy)benzoyloxy]benzoic acid and 2.48 g (30.2 mmol) of N-methylimidazole, and the mixture was stirred at room temperature for 1 hour. Then, while cooling the mixture with ice, a solution of 1.94 g (5.04 mmol) of (+)-N-methyl-L-tartarimide in 10 mL of tetrahydrofuran was added to the mixture. The mixture was stirred for 1 hour while cooling with ice, and was then stirred at room temperature for 16 hours. The solvent was then removed from the reaction solution by evaporation under reduced pressure, and the residue was refined twice through silica gel column chromatography (developing solvent used first: 1:3 (v/v) of ethyl acetate:hexane; developing solvent used second time: 1:10 (v/v) of ethyl acetate:hexane), to yield 0.98 g of a colorless solid substance (yield: 20.8%; melting point: 112.6° C.). Various analyses showed that the colorless solid substance was the target Compound No. 5.

The analyses results for the respective Compounds are shown in Tables 1 and 2 below.

TABLE 1

| | IR (neat)/cm$^{-1}$ | $[\alpha]^{20}_D$ (CHCl$_3$) |
|---|---|---|
| Compound No. 1 | 2940, 2861, 1722, 1625, 1481, 1469, 1405, 1392, 1272, 1193, 1101. | +153.5 (c 0.530) |
| Compound No. 2 | 2940, 2861, 1718, 1625, 1481, 1471, 1405, 1388, 1272, 1191, 1085. | +161.0 (c 0.480) |
| Compound No. 3 | 2940, 2861, 1724, 1625, 1481, 1471, 1407, 1388, 1272, 1191, 1081. | +163.4 (c 0.521) |
| Compound No. 4 | 2940, 2861, 1724, 1625, 1481, 1471, 1407, 1388, 1272, 1191, 1081. | −181.2 (c 0.536) |
| Compound No. 5 | 2942, 2861, 1731, 1602, 1510, 1409, 1257, 1205, 1160, 1060. | +143.8 (c 0.237) |

TABLE 2

| | $^1$H NMR (CDCl$_3$)/ppm |
|---|---|
| Compound No. 1 | 8.57 (s, 2H), 8.01 (dd, 2H, J = 8.8, 1.5 Hz), 7.82 (d, 2H, J = 9.1 Hz), 7.74 (d, 2H, J = 8.5 Hz), 7.49 (d, 2H, J = 7.3 Hz), 7.43-7.10 (m, 7H), 6.39 (dd, 2H, J = 17.4, 1.5 Hz), 6.12 (dd, 2H, J = 17.1, 10.4 Hz), 6.00 (s, 2H), 5.81 (dd, 2H, J = 10.4, 1.2 Hz), 4.89 (d, 1H, J = 14.6 Hz), 4.83 (d, 1H, J = 14.6 Hz), 4.18 (t, 4H, J = 6.4 Hz), 4.00 (t, 4H, J = 6.4 Hz), 1.88 (tt, 4H, J = 6.7, 6.7 Hz), 1.73 (tt, 4H, J = 7.3, 6.7 Hz), 1.62-1.43 (m, 8H). |
| Compound No. 2 | 8.58 (s, 2H), 8.02 (dd, 2H, J = 8.5, 1.2 Hz), 7.83 (d, 2H, J = 9.1 Hz), 7.74 (d, 2H, J = 8.5 Hz), 7.19 (dd, 2H, J = 8.8, 2.1 Hz), 7.13 (d, 2H, J = 2.4 Hz), 6.40 (dd, 2H, J = 17.4, 1.5 Hz), 6.12 (dd, 2H, J = 17.1, 10.4 Hz), 5.93 (s, 2H), 5.81 (dd, 2H, J = 10.4, 1.2 Hz), 4.18 (t, 4H, J = 6.4 Hz), 4.10 (t, 4H, J = 6.4 Hz), 3.77-3.62 (m, 2H), 1.88 (tt, 4H, J = 6.7, 6.7 Hz), 1.83-1.67 (m, 6H), 1.63-1.44 (m, 8H), 1.03 (t, 3H, J = 7.3 Hz). |
| Compound No. 3 | 8.58 (s, 2H), 8.01 (d, 2H, J = 8.5 Hz), 7.83 (d, 2H, J = 9.1 Hz), 7.75 (d, 2H, J = 8.5 Hz), 7.19 (dd, 2H, J = 9.1, 2.4 Hz), 7.13 (d, 2H, J = 1.8 Hz), 6.40 (dd, 2H, J = 17.1, 1.2 Hz), 6.12 (dd, 2H, J = 17.1, 10.4 Hz), 5.95 (s, 2H), 5.81 (dd, 2H, J = 10.4, 1.2 Hz), 4.18 (t, 4H, J = 6.7 Hz), 4.10 (t, 4H, J = 6.4 Hz), 3.23 (s, 3H), 1.88 (tt, 4H, J = 7.3, 6.7 Hz), 1.74 (tt, 4H, J = 7.3, 6.7 Hz), 1.63-1.47 (m, 8H). |
| Compound No. 4 | 8.57 (s, 2H), 8.01 (dd, 2H, J = 8.8, 1.8 Hz), 7.82 (d, 2H, J = 9.1 Hz), 7.74 (d, 2H, J = 8.5 Hz), 7.19 (dd, 2H, J = 9.1, 2.4 Hz), 7.13 (d, 2H, J = 2.4 Hz), 6.39 (dd, 2H, J = 17.7, 1.2 Hz), 6.12 (dd, 2H, J = 17.7, 10.4 Hz), 5.96 (s, 2H), 5.81 (dd, 2H, J = 10.4, 1.2 Hz), 4.18 (t, 4H, J = 6.7 Hz), 4.10 (t, 4H, J = 6.4 Hz), 3.23 (s, 3H), 1.88 (tt, 4H, J = 6.7, 6.7 Hz), 1.74 (tt, 4H, J = 7.3, 7.3 Hz), 1.63-1.42 (m, 8H). |
| Compound No. 5 | 8.16 (d, 4H, J = 9.1 Hz), 8.13 (d, 4H, J = 9.1 Hz), 7.34 (d, 4H, J = 8.5 Hz), 6.97 (d, 4H, J = 9.1 Hz), 6.40 (dd, 2H, J = 17.7, 1.2 Hz), 6.12 (dd, 2H, J = 17.7, 10.4 Hz), 5.88 (s, 2H), 5.82 (dd, 2H, J = 10.4, 1.2 Hz), 4.18 (t, 4H, J = 6.7 Hz), 4.05 (t, 4H, J = 6.4 Hz), 3.21 (s, 3H), 1.85 (tt, 4H, J = 6.9, 6.7 Hz), 1.73 (tt, 4H, J = 7.3, 6.7 Hz), 1.61-1.46 (m, 8H). |

Examples 2-1 to 2-5 and Comparative Example 1

Preparation of Polymerizable Composition and Polymer

Respective polymers were prepared according to the following procedures ((1) Preparation of Polymerizable Composition Solution and (2) Coating on Substrate and Curing).

(1) Preparation of Polymerizable Composition Solution

First, respective polymerizable compositions were prepared according to (i) and (ii) below.

(i) The above-described Compound No. 1 was blended to liquid crystal Compound No. 1 shown below at the percentages given in Table 3 shown further below.

(ii) Each of the above-described Compounds Nos. 1 to 5 or Comparative Compound No. 1 shown below was blended in an amount of 10% with Liquid Crystal Compound No. 1 shown below.

Then, 0.5 g of each polymerizable composition prepared as above was added to 1.0 g of 2-butanone (containing 375 ppm of "KH-40" (product of AGC Seimi Chemical Co., Ltd.) as a surfactant) and was completely dissolved with warm water. Then, 0.015 g of "N-1919" (product of Adeka Corporation), as a radical polymerization initiator, was added to the above mixture and dissolved completely therein. The mixture was passed through a 0.45-μm filter, to thus obtain respective polymerizable composition solutions.

[Chem. 32]

Liquid Crystal Compound No. 1

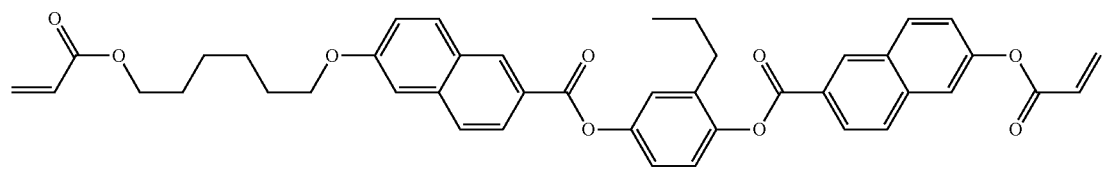

[Chem. 33]

Comparative Compound No. 1

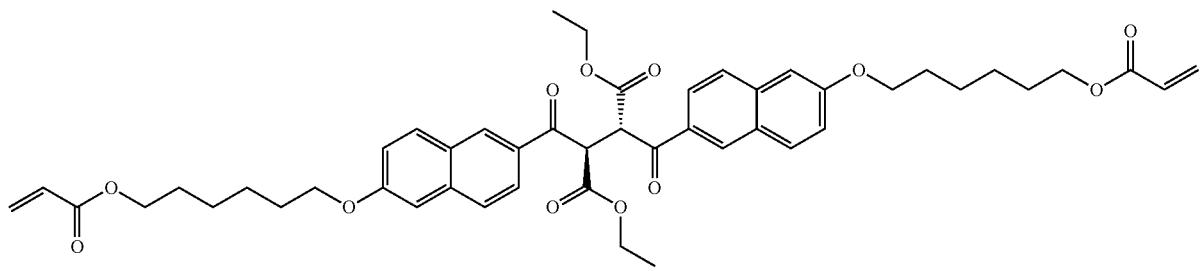

(2) Coating on Substrate and Curing

Using a spin coater (at 2000 rpm for 10 seconds), each polymerizable composition solution prepared in (1) above was coated on a glass substrate having a polyimide coating thereon and having undergone rubbing. The coated substrate was dried at 100° C. for 3 minutes using a hot plate. After drying, the substrate was cooled for 1 minute at room temperature. The substrate was then irradiated with rays of light equivalent to 300 mJ/cm$^2$ using a high pressure mercury lamp to cure the coating film, thus forming respective polymers of Examples 2-1 to 2-5 and Comparative Example 1.

Evaluation Example 1

Of the polymers prepared in Examples 2, the polymers prepared according to formulation (i) were evaluated for their selective reflection according to the following method. The evaluation results are shown in Table 3 below.

Selective Reflection Evaluation Method

The selective reflection was evaluated by measuring the reflectance at 25° C. within a wavelength range of 800 to 400 nm using a spectrophotometer (product of Hitachi High-Technologies Corporation; "U-3010" series) equipped with a 5° regular reflector, and finding the center wavelength of selective reflection (λ).

TABLE 3

| Compound No. 1 Blending Amount (%) | Selective Reflection (nm) |
| --- | --- |
| 5 | 969 |
| 7 | 728 |
| 10 | 504 |
| 12 | 422 |
| 15 | 360 |

Table 3 affirms that the selective reflection wavelengths can be changed by changing the blending amount of the present polymerizable optically-active imide compound. This fact shows that the present polymerizable optically-active imide compound is useful for various filters and C-plates.

Evaluation Example 2 and Comparative Evaluation Example 1

Of the polymers prepared in Examples 2 and Comparative Example 1, the polymers prepared according to formulation (ii) were evaluated for their selective reflection according to the method described above and were also evaluated for their orientation uniformity according to the following method. The evaluation results are shown in Table 4 below.

Orientation Uniformity Evaluation Method

The uniformity of each polymer prepared was evaluated using a polarizing microscope (product of Nikon Corporation; "Optiphot-2-Pol"). More specifically, the orientation uniformity was evaluated by setting a sample of each polymer on a stage and observing, with the eyes, the orientation state of the polymer while rotating the stage under crossed Nicols. Note that the evaluation criteria are as follows:

Good: Uniform selective reflection and no orientation deficiencies

Poor: Crystallization or orientation non-uniformity were observed

TABLE 4

| | Selective Reflection (nm) | Orientation Uniformity |
| --- | --- | --- |
| Compound No. 1 | 504 | Good |
| Compound No. 2 | 676 | Good |
| Compound No. 3 | 555 | Good |
| Compound No. 4 | 513 | Good |
| Compound No. 5 | 758 | Good |
| Comparative Compound No. 1 | Not Observed | Poor |

Table 4 shows that the polymer prepared using a polymerizable optically-active compound outside the present invention showed no selective reflection and showed whitish clouding caused by precipitation of the polymerizable optically-active compound and non-uniformity in orientation of the liquid crystal molecules. In contrast, the polymers prepared using the polymerizable optically-active imide compounds of the invention showed selective reflection and had uniform orientation across the entire film surface. This fact shows that the polymerizable optically-active imide compound of the invention is useful.

Evaluation Example 3

Of the polymers prepared according to formulation (ii) in Examples 2 above, the polymer obtained by blending Compound No. 3 and the polymer obtained by blending Compound No. 4 were bonded together, and the UV-Visible absorption spectrum of this bonded polymer was measured using a UV-Visible-NIR spectrophotometer (product of JASCO Corporation; "V-570"). The measured spectrum had a minimum transmittance value of 15.6% at 746 nm. This fact shows that, among the various polymers of the present invention, two enantiomeric polymers can be used one upon the other to find use as a cut-off filter that prevents transmission of light of a given wavelength.

Evaluation Example 4

Of the polymers prepared according to formulation (i) in Examples 2 above, the polymer prepared by blending 15% by mass of Compound No. 1 and a polymer prepared by blending 17% by mass of Compound No. 1 were evaluated for their retardation according to the following method. The evaluation results are shown in Table 5 below.

Retardation Evaluation Method

Retardation was measured using a polarizing microscope (product of Nikon Corporation; "Optiphot-2-Pol") with monochromatic light at 546 nm according to the Senarmont method. In this process, the substrate was set onto a mount whose tilt angle can be changed, and the retardation was measured at various tilt angles by changing the angle during measurement.

TABLE 5

| | Retardation (nm) | |
|---|---|---|
| Tilt Angle (°) | Compound No. 1 Blending Amount = 15% | Compound No. 1 Blending Amount = 17% |
| −50 | −62.9 | −58.5 |
| −40 | −45.2 | −47.6 |
| −30 | −28.4 | −28.1 |
| −20 | −12.6 | −13.2 |
| 0 | 0 | 0 |
| 20 | −12.3 | −12.7 |
| 30 | −22.9 | −26.5 |
| 40 | −43.1 | −40.6 |
| 50 | −62.3 | −56.0 |

Table 5 shows that the polymerizable optically-active imide compound of the invention can provide liquid crystal compositions having the targeted helical pitch. This fact shows that the polymers prepared using the polymerizable optically-active imide compounds of the invention are useful as optical retardation compensation materials for LCDs, such as negative C-plates.

The invention claimed is:

1. A polymerizable optically-active imide compound represented by general formula (I):

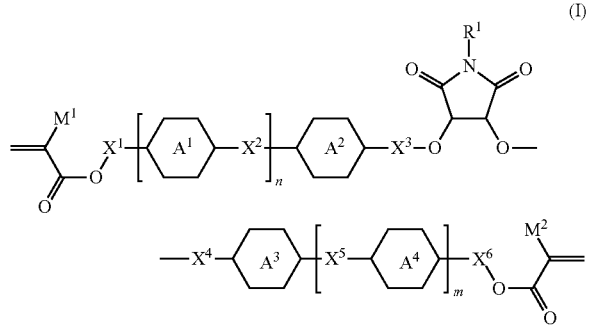

wherein, rings $A^1$, $A^2$, $A^3$, and $A^4$ each independently represent a benzene ring or a naphthalene ring, wherein a carbon atom in the benzene ring and the naphthalene ring may optionally be substituted by a nitrogen atom;

$M^1$ and $M^2$ each independently represent a hydrogen atom or a methyl group;

$R^1$ represents a $C_{1-10}$ alkyl group, a $C_{6-20}$ aryl group, or a $C_{7-20}$ arylalkyl group;

a hydrogen atom in $R^1$ may optionally be substituted by a halogen atom;

a methylene group in $R^1$ may be interrupted by —O—, —COO—, or —OCO—;

$X^1$ represents a direct bond, $-L^1-$, $-L^1O-$, $-L^1O-CO-$, $-L^1CO-O-$, or $-L^1O-CO-O-$;

$X^2$ and $X^5$ each independently represent a linking group consisting of a direct bond, an ester bond, an ether bond, a $C_{1-8}$ alkylene group that may be branched and that may have an unsaturated bond, or a combination thereof;

$X^3$ represents a direct bond, —CO—, $-L^2-$, $-OL^2-$, —O—COL²-, —CO—OL²-, or —O—CO—OL²-;

$X^4$ represents a direct bond, —CO—, $-L^1-$, $-L^1O-$, $-L^1O-CO-$, $-L^1CO-O-$, or $-L^1O-CO-O-$;

$X^6$ represents a direct bond, $-L^2-$, $-OL^2-$, —O—COL²-, —CO—OL²-, or —O—CO-OL²-;

$L^1$ and $L^2$ each independently represent a $C_{1-8}$ alkylene group that may be branched, wherein the $C_{1-8}$ alkylene group may be interrupted one to three times by an oxygen atom; and n and m each independently represent 0 or 1.

2. The polymerizable optically-active imide compound according to claim 1, wherein each of $X^3$ and $X^4$ in general formula (I) is —CO—.

3. The polymerizable optically-active imide compound according to claim 1, wherein each of rings $A^2$ and $A^3$ in general formula (I) is a naphthalene ring.

4. The polymerizable optically-active imide compound according to claim 1, wherein each of rings $A^1$, $A^2$, $A^3$, and $A^4$ in general formula (I) is a benzene ring.

5. The polymerizable optically-active imide compound according to claim 1, wherein each of $M^1$ and $M^2$ in general formula (I) is a hydrogen atom.

6. The polymerizable optically-active imide compound according to claim 1, wherein, in general formula (I), rings $A^1$ and $A^4$, as well as rings $A^2$ and $A^3$, are the same ring, groups $M^1$ and $M^2$, $X^1$ and $X^6$, $X^2$ and $X^5$, as well as $X^3$ and $X^6$ are the same group in each pair, and n and m are the same number.

7. A polymerizable composition comprising the polymerizable optically-active imide compound according to claim 1.

8. The polymerizable composition according to claim 7, further comprising a liquid crystal compound.

9. The polymerizable composition according to claim 8, wherein the polymerizable optically-active imide compound is present at a concentration of to 50 parts by mass when a total of the polymerizable optically-active imide compound and the liquid crystal compound is 100 parts by mass.

10. The polymerizable composition according to claim 8, wherein the liquid crystal compound has a polymerizable functional group.

11. The polymerizable composition according to claim 7, wherein the composition exhibits a cholesteric phase.

12. A polymer prepared by photopolymerization of the polymerizable composition according to claim 7.

13. The polymer according to claim 12, wherein the polymer exhibits optical anisotropy.

14. An optical film made using the polymer according to claim 12.

15. An optical retardation compensation material for liquid crystal displays, made using the optical film according to claim 14.

16. A cut-off filter made using the optical film according to claim 14.

17. The polymerizable optically-active imide compound according to claim 2, wherein each of rings $A^2$ and $A^3$ in general formula (I) is a naphthalene ring.

18. The polymerizable optically-active imide compound according to claim 2, wherein each of rings $A^1, A^2, A^3$, and $A^4$ in general formula (I) is a benzene ring.

19. The polymerizable optically-active imide compound according to claim 2, wherein each of $M^1$ and $M^2$ in general formula (I) is a hydrogen atom.

20. The polymerizable optically-active imide compound according to claim 3, wherein each of $M^1$ and $M^2$ in general formula (I) is a hydrogen atom.

21. The polymerizable optically-active imide compound according to claim 1, wherein $R^1$ in general formula (I) represents a $C_{1-10}$ alkyl group or a $C_{7-20}$ arylalkyl group.

22. The polymerizable optically-active imide compound according to claim 1, wherein $R^1$ in general formula (I) represents methyl, ethyl, propyl, butyl, amyl or benzyl.

23. The polymerizable optically-active imide compound according to claim 1, selected from the group consisting of:

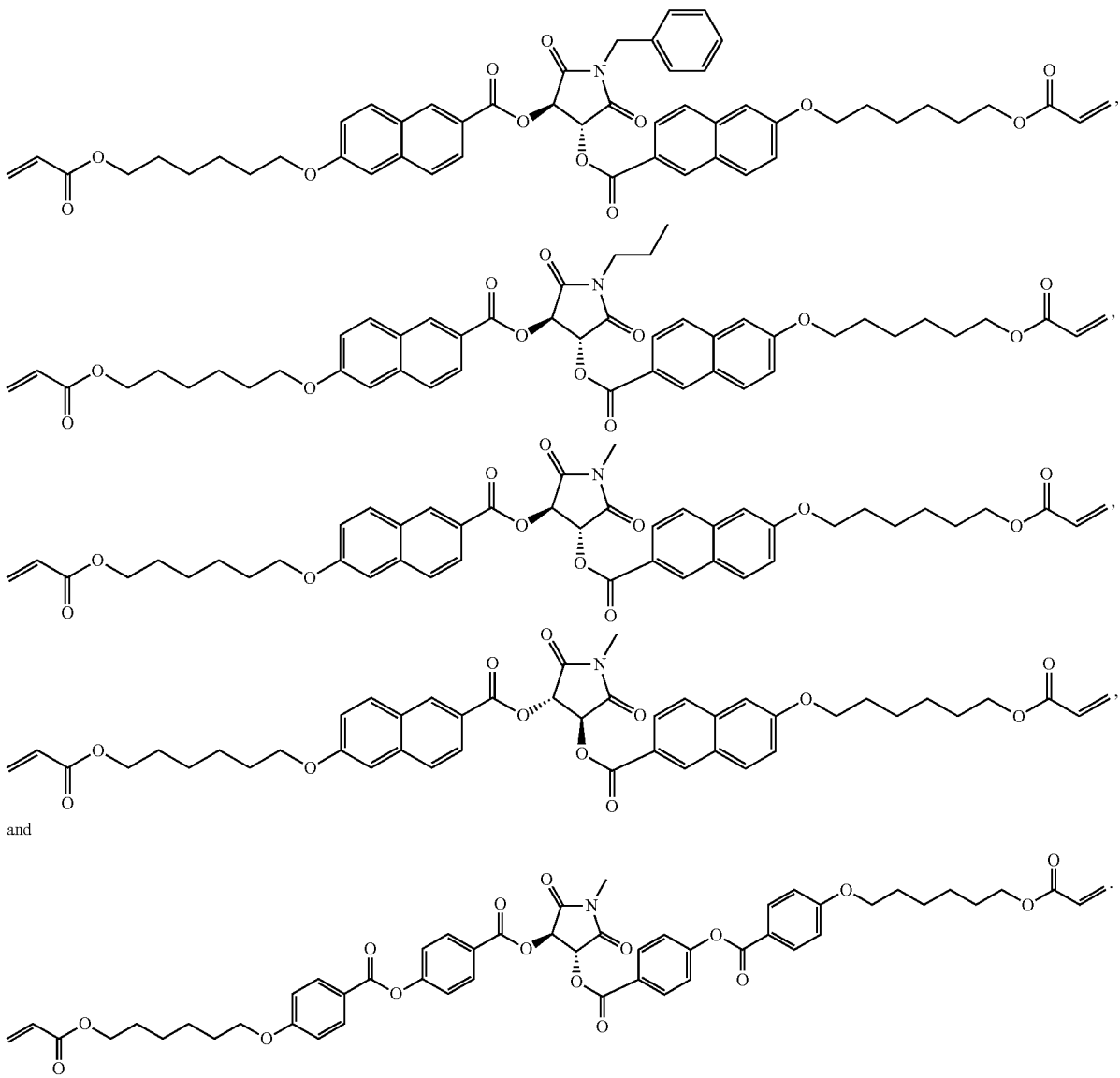

and

* * * * *